US008483456B2

(12) United States Patent
Nagatsuka et al.

(10) Patent No.: US 8,483,456 B2
(45) Date of Patent: Jul. 9, 2013

(54) DYNAMIC IMAGE PROCESSING SYSTEM

(75) Inventors: Sumiya Nagatsuka, Hino (JP);
Yoshihiro Takeda, Hino (JP)

(73) Assignee: Konica Minolta Medical & Graphic, Inc. (JP)

( * ) Notice: Subject to any disclaimer, the term of this patent is extended or adjusted under 35 U.S.C. 154(b) by 394 days.

(21) Appl. No.: 12/815,532

(22) Filed: Jun. 15, 2010

(65) Prior Publication Data

US 2010/0246925 A1    Sep. 30, 2010

Related U.S. Application Data

(63) Continuation of application No. PCT/JP2008/072243, filed on Dec. 8, 2008.

(30) Foreign Application Priority Data

Dec. 19, 2007  (JP) .................................. 2007-326875
Dec. 26, 2007  (JP) .................................. 2007-334523

(51) Int. Cl.
*G06K 9/00*    (2006.01)

(52) U.S. Cl.
USPC ......................................................... 382/128

(58) Field of Classification Search
USPC ......................................................... 382/128
See application file for complete search history.

(56) References Cited

U.S. PATENT DOCUMENTS 6,135,959 A     10/2000  Murashita et al.
7,155,042 B1 *  12/2006  Cowan et al. ................. 382/128
7,593,554 B2 *   9/2009  Miller et al. .................. 382/128
2003/0190064 A1 * 10/2003  Inoue ............................ 382/128
2006/0239530 A1  10/2006  Oosawa

FOREIGN PATENT DOCUMENTS

| EP | 0934724 A1 | 8/1999 |
| EP | 1350468 A2 | 10/2003 |
| JP | 7-37061 A | 2/1995 |
| JP | 11-221210 A | 8/1999 |
| JP | 2003-10171 A | 1/2003 |
| JP | 2003-70781 A | 3/2003 |
| JP | 2004-410 A | 1/2004 |

(Continued)

OTHER PUBLICATIONS

International Search Report for International Application No. PCT/JP2008/072243 with English translation mailed Mar. 10, 2009.

*Primary Examiner* — Tom Y Lu
(74) *Attorney, Agent, or Firm* — Cantor Colburn LLP

(57) ABSTRACT

It is possible to improve a diagnostic performance by a dynamic image and in particular, to provide information effective for diagnosis of the lung ventilation function. Provided is a dynamic image capturing system including: a calculation device which calculates a dynamic feature amount according to a plurality of frame images of the dynamic image captured by an imaging device; and a diagnosis console which displays the frame images of the captured dynamic image as a dynamic image display or a still image display on a display screen of a display unit and colors at least one of the frame images with a color in accordance with a calculation result of a feature amount obtained by the calculation device. In the diagnosis of the lung ventilation function, the breast portion of an examinee is dynamically imaged over a plurality of time phases to calculate a feature amount and an estimated ventilation amount at each of the time phases, so that the calculation results are displayed on the display screen.

12 Claims, 21 Drawing Sheets

FOREIGN PATENT DOCUMENTS

| | | |
|---|---|---|
| JP | 2004-305487 A | 11/2004 |
| JP | 2004-312434 A | 11/2004 |
| JP | 2004-313551 A | 11/2004 |
| JP | 2005-28121 A | 2/2005 |
| JP | 2006-239195 A | 9/2006 |
| JP | 3931792 B2 | 8/2007 |

* cited by examiner

DYNAMIC IMAGE PROCESSING SYSTEM

CROSS REFERENCE TO RELATED APPLICATIONS

This is a Continuation of International Application No. PCT/JP2008/072243, filed on Dec. 8, 2008. Priority under 35 U.S.C. §119(a) and 35 U.S.C. §365(b) is claimed from Japanese Applications Nos. 2007-326875, filed Dec. 19, 2007; and 2007-334523 filed Dec. 26, 2007; the disclosures of each of which are also incorporated herein by reference.

TECHNICAL FIELD OF THE INVENTION

The present invention relates to dynamic image processing systems.

PRIOR ART

Conventionally, various types of technologies are known that provide diagnostic information on still images imaged using films/screens or photostimulable phosphor plates. For example, in Patent Document 1 is described a technology in which a difference image is acquired between still images acquired in a time series by imaging the same part of the same examinee, color information is added to the difference image for displaying the progress or curing of a disorder in the difference image, and superimposing it on the still images. This technology is one that makes it possible to display the extent of progress or curing of a disorder relatively, and is a desirable form in film diagnosis.

However, in recent years, compared to diagnosis using still images, attempts are being made to image dynamic images of the target parts of examination using semiconductor image sensors such as FPDs (Flat Panel Detectors), and apply them to diagnosis. In concrete terms, using the fastness of response of semiconductor image sensors in reading and erasing image data, matching with the timing of reading and erasing image data by semiconductor image sensors, pulse shaped radiation beams are emitted successively from the radiation source, imaging is done a plural number of times in one second, thereby acquiring dynamic images of the target part of examination. By displaying successively the sequence of a plurality of images acquired by imaging, the doctor can recognize a sequence of movements of the examination target part.

Various types of technologies have also been proposed for displaying dynamic images in an easy to view manner. For example, in Patent Document 2, a technology is described in which the dynamic images acquired successively in a time series are handled as a "time and space 3-dimensional image" with the time taken along the depth direction, and its transverse image and sagittal image are prepared, and displayed in an observable manner. Further, in Patent Document 3, a technology has been described in which inter-frame difference images are prepared of dynamic images, and a difference dynamic image is displayed.

Further, apparatuses have also been proposed which carry out image analysis of X-ray images, etc., and detect image areas that are presumed to be of affected parts (see, for example, Patent Document 4). In order to provide information to serve as useful reference when the doctor observes the X-ray image, etc., and judges the part as normal or abnormal, in this kind of apparatus displays are made of indicating potential areas of affected parts detected in the X-ray images, etc.

There is also a method in which the density changes are quantified by converting density distribution into a graph, and displaying as information necessary for diagnosis. It is very common that density changes are present in affected parts compared to normal tissue parts, and diagnosis is assisted by providing information related to such density changes to the doctor.

Patent Document 1: Japanese Patent No. 3931792
Patent Document 2: Japanese Unexamined Patent Application Publication No. 2004-305487
Patent Document 3: Japanese Unexamined Patent Application Publication No. 2004-312434
Patent Document 2: Japanese Unexamined Patent Application Publication No. Hei 7-37061

DISCLOSURE OF THE INVENTION

Problems to be Solved by the Invention

When dynamic image display is made by successively switching a sequence of images constituting a dynamic image, although the doctor can grasp the sequence of movements of the target part under examination, for example, whether or not the expansion and contraction of the pulmonary field is being made, grasping whether those movements are normal or abnormal, for example, grasping whether the respiration is sufficient (whether the ventilation volume of the lungs is sufficient) or not is difficult.

Although, in a large hospital, since a high resolution viewer apparatus with a large size is used and the image of the patient is displayed close to life size (actual size), there are situations in which the doctor can recognize instinctively whether or not normal movements are being made from the dynamic images based on experience, etc., when carrying out diagnosis using a monitor sold generally in market it is impossible to display the entire image of the imaged body in life size, and since the diagnosis has to be made using a reduced size display of the images by carrying out decimating processing, it is difficult for the doctor to recognize instinctively whether or not normal movements are being made from the dynamic images.

However, as has been described in Patent Documents 1 and 2 above, if only the information extracted from the dynamic images for diagnosis is displayed, it is not possible to graphs the sequence of operations of the target part under examination.

Further, regarding the respiratory function of the lungs, not only the localized affected part that is the cause of lowering of the function, but also observations such as the ventilation volume, etc., can become important for diagnosis. Therefore, in the conventional method of detecting and displaying only the affected parts, it cannot be said that sufficient diagnostic support is being given for the ventilation function.

An object of the present invention is to enhance the diagnostic performance using dynamic images. In particular, it is to provide information useful for the diagnosis of the respiratory function of lungs.

Means for Solving the Problems

In order to solve the above problems, at least an embodiment of a dynamic image processing system may include:
an imaging unit that carries out dynamic imaging of a target part of a human body under examination and generates a plurality of frames of images indicating a dynamic condition of the target part of the human body under examination; and
a calculation unit that calculates from said frames of images a dynamic feature amount of the target part of the human body under examination.

At least an embodiment may also include:

a display unit that displays on a display screen the plurality of frames of images; and a display control unit that, according to a result of calculation of the dynamic feature amount by said calculation unit, adds information to at least one among the plurality of frames of images, or modifies a part of at least one among the plurality of frames of images, and displays on said display screen.

In at least an embodiment, said display control unit, according to the result of calculation of the feature quantity by said calculation device, colors at least one among said plurality of frames of images and displays on said display screen.

In at least an embodiment, said display control unit has a dynamic image display mode for a motion display of the plurality of frames of images indicating a dynamic condition on the display screen, and a still image display mode for a still image display of the plurality of frames of images indicating a dynamic condition arranging the plurality of frame of images next to one another on the display screen, and wherein the dynamic image processing system is provided with an operation unit for selecting the dynamic image display mode or the still image display mode.

In at least an embodiment, said calculation unit calculates, as the dynamic feature amount, an area ratio of an image region of the target part under examination between neighboring frame images among the plurality of frames of images in the imaging sequence; and said display control unit, when the dynamic image display mode is selected, displays a motion image of the plurality of frames of images indicating dynamic condition on the display screen, and colors the frame image currently being displayed in the motion image according to the area ratio calculated by said calculation unit between the frame image currently being displayed and a frame image imaged immediately prior to it and displays the colored frame image alongside the motion image being displayed.

In at least an embodiment, said calculation unit, among the plurality of frames of images, extracts a frame image with a maximum area of an image region of the target part under examination and a frame image with a minimum area of an image region of the target part, and calculates as the feature amount the area ratio of the image region of the target part between the extracted frame images; and wherein said display control unit, when the dynamic image display mode is selected, not only displays a motion image of the plurality of frames of images indicating dynamic condition on the display screen, but also colors the frame image with the maximum area or the frame image with the minimum area according to the area ratio calculated by said calculation unit and displays the colored frame image alongside the motion image being displayed.

In at least an embodiment, said calculation unit calculates, as the dynamic feature amount, an area ratio of an image region of the target part under examination between neighboring frame images among the plurality of frames of images in the imaging sequence; said operation unit is configured so that, when the still image display mode is selected, in addition, it is possible to specify one frame image among the plurality of frames of images displayed next to one another; and said display control unit, when the still image display mode is selected, makes a still image display of the plurality of frames of images indicating the dynamic motion arranged next to one another and, and colors and displays the specified frame image with a color corresponding to the area ratio calculated by said calculation unit between the frame image and a frame image imaged immediately prior to it.

In at least an embodiment, said calculation unit calculates, as the dynamic feature amount, an area ratio of an image region of the target part under examination between neighboring frame images among the plurality of frames of images in the imaging sequence; and said display control unit displays a motion image of the plurality of frames of images indicating dynamic condition on the display screen, and colors the frame image currently being displayed in the motion image according to the area ratio calculated by said calculation unit between the frame image currently being displayed and a frame image imaged immediately prior to it and displays the colored frame image alongside the motion image being displayed.

In at least an embodiment, said calculation unit, among the plurality of frames of images, extracts a frame image with a maximum area of an image region of the target part under examination and a frame image with a minimum area of an image region of the target part, and calculates as the feature amount the area ratio of the image region of the target part between the extracted frame images; and said display control unit displays a motion image of the plurality of frames of images indicating dynamic condition on the display screen of the display unit, and colors frame image with a maximum area of an image region of the target part under examination or the frame image with a minimum area of an image region of the target part according to the area ratio calculated by said calculation unit and displays the colored frame image alongside the motion image being displayed.

At least an embodiment may also include an operation unit; and wherein said calculation unit calculates, as the dynamic feature amount, an area ratio of an image region of the target part under examination between neighboring frame images among the plurality of frames of images in the imaging sequence; and wherein said display control unit makes a still image display of the plurality of frames of images indicating the dynamic motion arranged next to one another and, and colors and displays the frame image specified by the operation unit with a color corresponding to the area ratio calculated by said calculation unit between the frame image and a frame image imaged immediately prior to it.

In at least an embodiment, said display control unit reduces the sizes of the plurality of frames of images and displays them in the display screen of said display unit.

In at least an embodiment, the plurality of frames of images is frames showing a dynamic motion of a chest part including a pulmonary field; and said calculation unit calculates a ventilation ratio of the pulmonary field by calculating as the feature amount the area ratio between the plurality of frames of images.

In at least an embodiment, said imaging unit carries out dynamic imaging of a chest region of a human body and generates for at least one respiration phase a plurality of frames of images indicating a dynamic condition in a plurality of time phases, wherein said calculation unit, acquires information of an absolute ventilation volume between a maximum aspiratory level and a maximum inspiratory level during the respiration phase, calculates an estimated ventilation volume per unit change quantity of a signal from the absolute ventilation volume and a quantity of signal value change between the dynamic image of the maximum aspiratory level and the dynamic image of the maximum inspiratory level among the generated plurality of frames of images indicating a dynamic condition, using a value of the estimated ventilation volume per unit change quantity in the signal calculates each estimated ventilation volume at each time phase, and wherein said display control unit displays in said display unit the calculated each estimated ventilation volume for each time phase.

In at least an embodiment, said display control unit displays a numerical value indicating the calculated estimated ventilation volume.

In at least an embodiment, said display control unit generates a pictorial image indicating the calculated estimated ventilation volume in the pulmonary field region in each frame of images indicating dynamic condition, and displays the pictorial images by switching them successively according to the time phase.

In at least an embodiment, wherein said calculation unit divides the pulmonary field region included in the dynamic images into a plurality of regions, and calculates the estimated ventilation volume for each of these divided regions, and wherein said display control unit displays said estimated ventilation volume calculated for each of said divided regions in said dynamic images.

Effect of the Invention

According to at least an embodiment, the doctor can grasp the feature quantity of dynamic movement in the dynamic images while observing the imaged dynamic images and it is possible to increase the performance of diagnosis using dynamic images.

According to at least an embodiment, since the doctor can select whether to make a dynamic image display or still image display of the sequence of frame images constituting a dynamic image, it is possible to display the dynamic images in a form that is easy for the doctor to diagnose.

According to at least an embodiment, it becomes possible for the doctor to grasp easily whether the target part of examination is functioning sufficiently or not at the timing of imaging the frame images being displayed in the display screen.

According to at least an embodiment, it becomes possible for the doctor to grasp easily whether the target part of examination on the whole is functioning sufficiently or not.

According to at least an embodiment, it becomes possible for the doctor to grasp easily whether the target part of examination is functioning sufficiently or not at the timing of imaging the frame image of interest.

According to at least an embodiment, it is possible to increase the performance of diagnosis due to dynamic images reduced in size.

According to at least an embodiment, it is possible for the doctor to grasp easily from the dynamic images whether the ventilation volume of pulmonary field is sufficient or not.

According to at least an embodiment, it is possible to provide the information of the estimated ventilation volume at each time phase of imaging the dynamic images. At the time of diagnosing the ventilation function by observing the dynamic images, the doctor can use the information of the estimated ventilation volume as useful reference information.

According to at least an embodiment, it is possible to grasp the estimated ventilation volume in a concrete numerical value.

According to at least an embodiment, it is possible to grasp visually the change in the estimated ventilation volume with the passage of time.

According to at least an embodiment, it is possible to grasp the estimated ventilation volume that is changing for each region. Since with a measuring instrument it is only possible to measure the ventilation volume of the lungs as a whole, at the time of diagnosing by focusing the attention on the region where the ventilation function has decreased, the information of the estimated ventilation volume of each region is particularly useful.

BRIEF DESCRIPTIONS OF THE DRAWINGS

DESCRIPTIONS OF SYMBOLS

Figure 1:
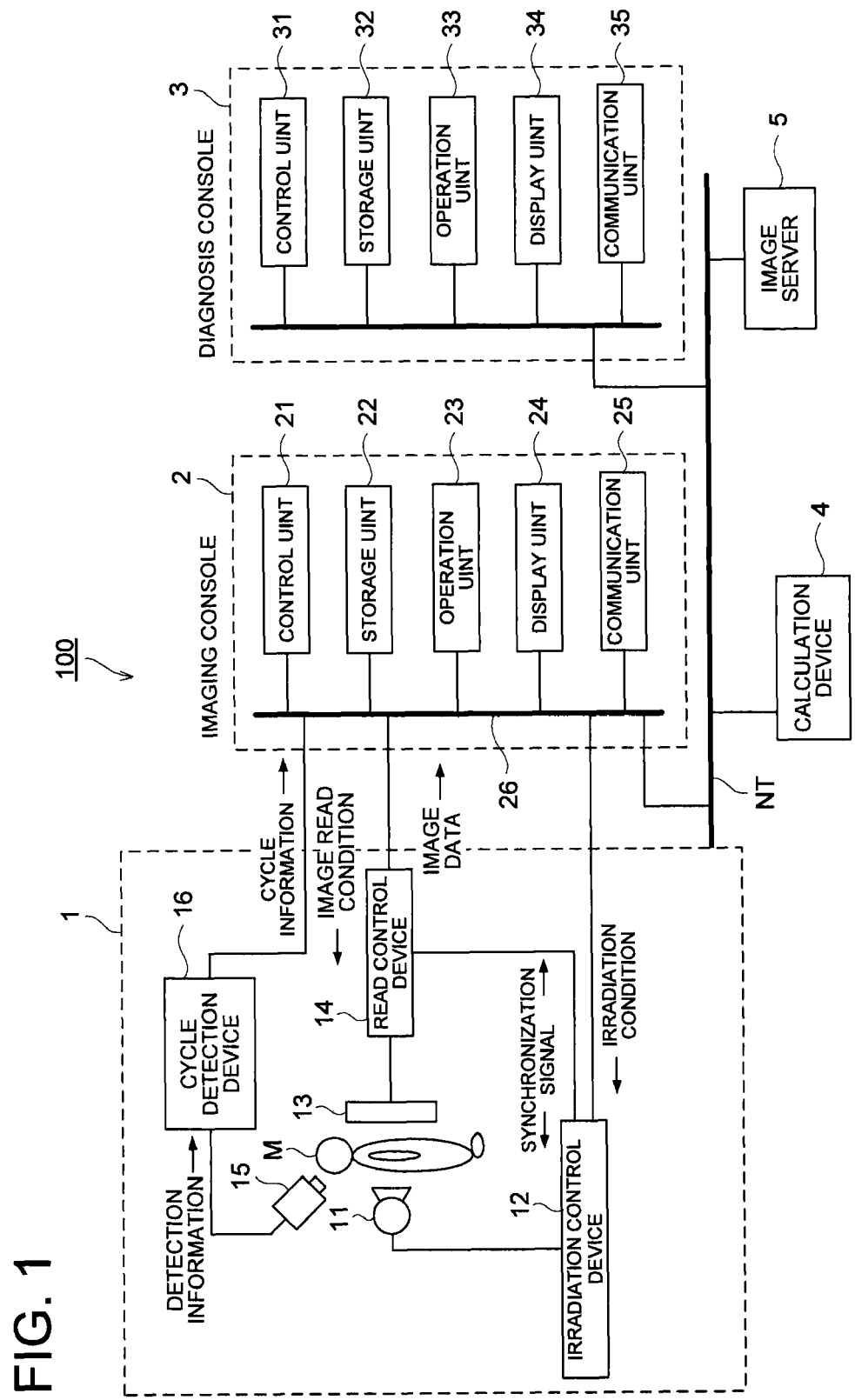
FIG. 1 is a diagram showing an example of the overall configuration of a dynamic image processing system according to a preferred embodiment of the present invention.

100 Dynamic image processing system
1 Imaging device

11 Radiation source
12 Irradiation control device
13 Radiation detection unit
14 Reading control unit
15 Cycle detection sensor
16 Cycle detection device
2 Imaging console
21 Control unit
22 Storage unit
23 Operation unit
24 Display unit
25 Communication unit
26 Bus
3 Diagnosis console
31 Control unit
32 Storage unit
33 Operation unit
34 Display unit
35 Communication unit
36 Bus
4 Calculation device
41 Control unit
42 Storage unit
43 Communication unit
44 Bus
45 Communication unit
46 Image processing unit
47 Image analysis unit
48 Control unit
49 Operation unit
5 Image server
50 Display unit
51 Storage unit

DETAILED DESCRIPTION OF THE PREFERRED EMBODIMENT

A preferred embodiment of the present invention is explained below. However, the present invention shall not be limited to the examples shown in the figures.

[Configuration of the Dynamic Image Processing System 100]

To begin with, the configuration is described below.

FIG. 1 shows an overall configuration of a dynamic image processing system 100 according to a preferred embodiment of the present invention.

As shown in FIG. 1, the dynamic image processing system 100 is configured by connecting an imaging device 1 and an imaging console 2 via communication cables, etc., and connecting via a communication network NT such as a LAN (Local Area Network) the imaging console 2, a diagnosis console 3, a calculation device 4, and an image server 5. The different devices constituting the dynamic image processing system 100 conform to the DICOM (Digital Image and Communications in Medicine) standards, and the communication between the different devices is carried out according to DICOM rules.

[Configuration of the Imaging Device 1]

The imaging device 1 is a device that images the dynamic movements of the human body having periodicity (cycles), for example, the shape changes of expansion and contraction of the lungs due to respiration, pulsation of the heart, etc. Dynamic imaging is carried out by emitting radiation continuously to the target part of examination and acquiring a plurality of images (that is, successive imaging). The sequence of images acquired by this successive imaging is called dynamic imaging. Further, the each of the plurality of images constituting a dynamic image is called a frame image.

The imaging device 1, as shown in FIG. 1, is configured by providing it with a radiation source 11, an irradiation control device 12, a radiation detection device 13, a read control device 14, a cycle detection sensor 15, a cycle detection device 16, etc.

The radiation source 11 emits X-rays towards the imaged body M according to the control of the irradiation control device 12.

The irradiation control device 12 is connected to the imaging console 2, and carries out radiography by controlling the radiation source 11 based on the irradiation conditions input from the imaging console 2. The irradiation conditions input from the imaging console 2, for example, during successive irradiation, are the pulse rate, the pulse width, the pulse interval, timings of imaging starting and ending, X-ray tube current value, X-ray tube voltage value, filter type, etc. The pulse rate is the number of times of irradiation per second and matches with the frame rate described later. The pulse width is the duration of irradiation during one irradiation. The pulse interval, during successive imaging, is the time interval between the starting of one irradiation and the starting of the next irradiation, and matches with the frame interval described later.

The radiation detection device 13 is constituted by a semiconductor image sensor such as an FPD, etc. An FPD, for example, has a glass substrate, and at a prescribed position on the substrate, has a plurality of pixels in the form of a matrix that detect the radiation that is emitted from the radiation source 11 and has at least passed through the imaged body M according to its strength, convert and accumulate the detected radiation into electrical signals. Each pixel is constituted from a switching device such as a TFT (Thin Film Transistor), etc.

The read control device 14 is connected to the imaging console 2. The read control device 14 controls the switching devices of the different pixels of the radiation detection device 13 based on the image read conditions input from the imaging console 2, switches the reading of the electrical signal accumulated in each pixel, and acquires the image data by reading the electrical signals accumulated in the radiation detection device 13. Next, the reading control device 14 outputs the acquired image data to the imaging console 2. The image reading conditions are, for example, the frame rate, frame interval, pixel size, image size (matrix size), etc. The frame rate is the number of frame images acquired per second, and matches with the pulse rate. The frame interval, in successive imaging, is the time interval from the starting of the operation of acquiring one frame image to the starting of acquiring the next frame image, and matches with the pulse interval.

Here, the irradiation control device 12 and the read control device 14 are connected mutually, and exchange synchronization signals between each other thereby synchronizing the irradiation operation and the image reading operation.

The cycle detection sensor 15 detects the state of the examination target part of the imaged body M and outputs the detection information to the cycle detection device 16. As a cycle detection sensor 15, for example, when the examination target parts are the lungs (ventilation), it is possible to apply a respiration monitor belt, a CCD (Charge Coupled Device) camera, optical camera, spirometer, etc. In addition, when the examination target part is the heart (blood flow), it is possible to use an electrocardiograph.

The cycle detection device 16, for example, based on the detection information input from the cycle detection sensor 15, detects the number of cycles of the dynamic movements of the examination target part, and detects which state within a cycle is the examination target part in currently, and outputs the detection result (cycle information) to the control unit 21 of the imaging console 2. Here, the cycle number, in more detail, is the number of cycles per unit time, and, for example, when the examination target parts are the lungs (ventilation), it is the number of respirations (per second), and in the case of the heart (blood flow), it is the pulse rate (heart beats per second).

The cycle detection device 16, for example, when the examination target parts are the lungs (ventilation), takes as the reference point of one cycle the time at which the detection information from the cycle detection sensor 15 (respiration monitor belt, a CCD camera, optical camera, spirometer, etc.) is input indicating that the state of the lungs has changed from aspiration to inspiration, and recognizes the period until this state is detected next as one cycle.

Further, the cycle detection device 16, when the examination target part is the heart, takes the time when the R wave is input from the cycle detection sensor 15 (electrocardiograph, etc.,) as the reference point, and recognizes as one cycle the time until the R wave is detected next.

Next, the number of cycles recognized per second is detected as the number of cycles.

[Configuration of the Imaging Console 2]

The imaging console 2 not only outputs the irradiation conditions and the image reading conditions to the imaging device 1 and controls the radiography and X-ray image reading operations by the imaging device 1, but also, displays for confirmation the image data acquired from the imaging device 1 for the technician to confirm the positioning and for confirming whether or not the image is suitable for diagnosis.

The imaging console 2, as shown in FIG. 1, is configured from a control unit 21, a storage unit 22, an operation unit 23, a display unit 24, and a communication unit 25, and each of these units is connected to a bus 26.

The control unit 21 is configured from a CPU (Central Processing Unit), a RAM (Random Access Memory), etc. The CPU of the control unit 21, according to the operations of the operation unit 23, reads out the system program or various types of processing programs stored in the storage unit 22 and loads them into the RAM, and carries out central control of the operations of the different parts of the imaging console 2, the irradiation operation and the image reading operation of the imaging device 1 according to the loaded programs. Further, a timer not shown in the figure is connected to the control unit 21.

The storage unit 22 is configured using a nonvolatile semiconductor memory or a hard disk, etc. The storage unit 22 stores various types of programs executed in the control unit 21, the parameters necessary for executing the processing based on the programs, and stores data such as the result of processing, etc. For example, the storage unit 22 stores the imaging control processing program for carrying out the control of the imaging flow shown in FIG. 3. Further, the storage unit 22 stores the irradiation conditions and the image reading conditions corresponding to the examination target parts. Various types of programs are stored in the readable program code form, and the control unit 21 successively executes the operations following these program codes.

The operation unit 23 is configured by providing it with a keyboard having cursor keys, numeral input keys, and various types of function keys, etc., a pointing device such as a mouse, etc., and the instruction signals input using key operations in the keyboard and mouse operations are output to the control unit 21. Further, the operation unit 23 can also have a touch panel provided on the displays screen of the display unit 24, and in this case, the instruction signals input via the touch panel are output to the control unit 21.

The display unit 24 is configured using an LCD (Liquid Crystal Display) or a CRT (Cathode Ray Tube) monitor, and displays the input instructions from the operation unit 23 or data, etc., following the instructions of the display signal input by the control unit 21.

The communication unit 25 is provided with a LAN adapter, a modem, or a TA (Terminal Adapter), etc., and controls the data transmission and reception between the different apparatuses connected to the communication network NT

[Configuration of the Diagnosis Console 3]

The diagnosis console 3 is a terminal for acquiring dynamic image data from the image server 5, displaying dynamic images based on the acquire image data, so that the doctor can carry out image diagnosis.

The diagnosis console 3, as shown in FIG. 1, is configured from a control unit 31, a storage unit 32, an operation unit 33, a display unit 34, and a communication unit 35, and each of these units is connected to a bus 36.

The control unit 31 is configured from a CPU, a RAM, etc. The CPU of the control unit 31, according to the operations of the operation unit 33, reads out the system program or various types of processing programs stored in the storage unit 32 and loads them into the RAM, and executes various types of processings such as the display control processing described later according to the loaded programs, and carries out central control of the operations of the different parts of the diagnosis console 3.

The storage unit 32 is configured using a nonvolatile semiconductor memory or a hard disk, etc. The storage unit 32 stores various types of programs such as the display control program executed in the control unit 31, the parameters necessary for executing the processing based on the programs, and stores data such as the result of processing, etc. Various types of programs are stored in the readable program code form, and the control unit 31 successively executes the operations following these program codes.

The operation unit 33 as an operation section is configured by providing it with a keyboard having cursor keys, numeral input keys, and various types of function keys, etc., a pointing device such as a mouse, etc., and the instruction signals input using key operations in the keyboard and mouse operations are output to the control unit 31. Further, the operation unit 33 can also have a touch panel provided on the displays screen of the display unit 34, and in this case, the instruction signals input via the touch panel are output to the control unit 31.

The display unit 24 as a display section is configured using an LCD or a CRT monitor, and displays the input instructions from the operation unit 33 or data, etc., following the instructions of the display signal input by the control unit 31.

The communication unit 35 is provided with a LAN adapter, a modem, or a TA etc., and controls the data transmission and reception between the different apparatuses connected to the communication network NT.

[Configuration of the Calculation Device 4]

Next, the calculation device 4 and the image server 5 are explained.

The calculation device 4 and the image server 5 are used for providing the X-ray image acquired by imaging.

Figure 2:
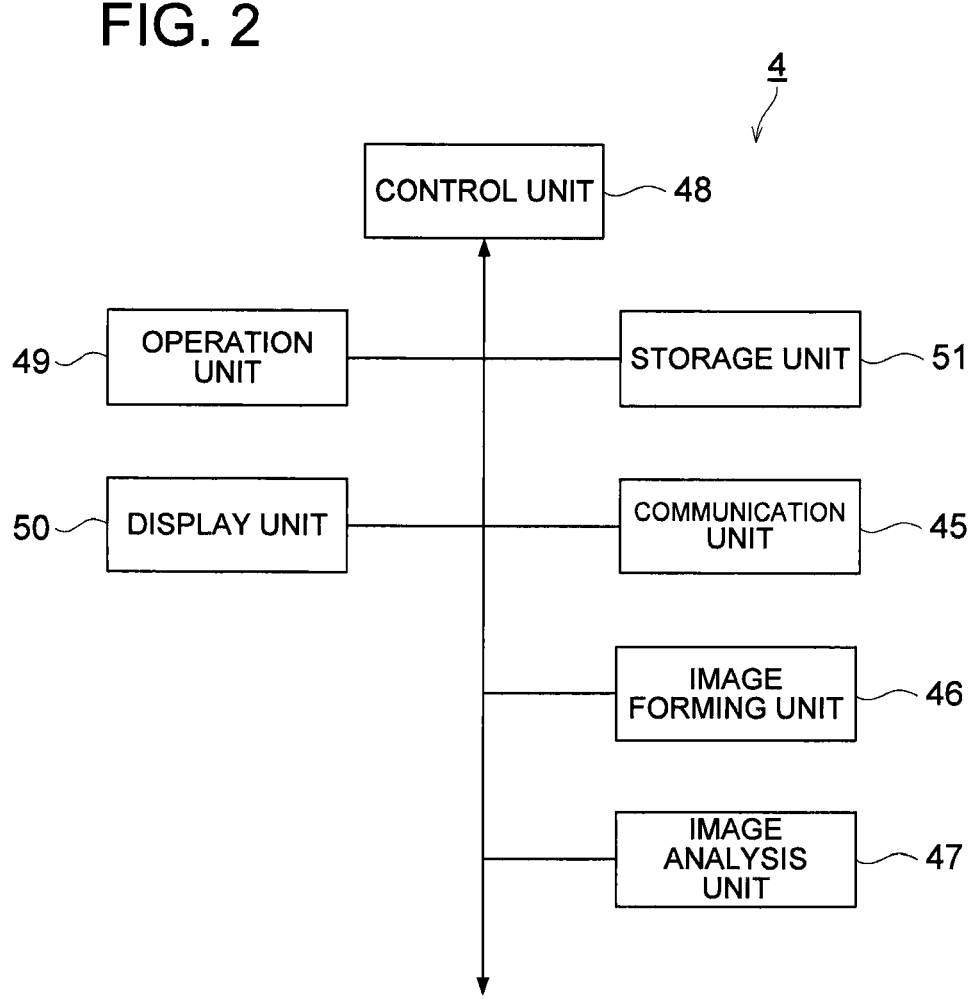
FIG. 2 is a diagram showing the functional configuration of the calculation device of FIG. 1.

The calculation device 4 is explained referring to FIG. 2.

The calculation device 4 carries out image processing on the X-ray images so that the image quality becomes one that makes it easy for the doctor to observe. As shown in FIG. 2, the calculation device 4 is configured from a control unit 48, an operation unit 49, a display unit 50, a storage unit 51, a communication unit 45, an image processing unit 46, and an image analysis unit 47.

Regarding the communication unit 45, the control unit 48, the operation unit 49, the display unit 50, and the storage unit 51 are basically the same as the control unit 21 to the communication unit 25 of the imaging console 2 described above, their detailed explanations will be omitted here.

The image processing unit 46 carries out various types of image processing on the X-ray image such as gray scale conversion processing, frequency adjustment processing, etc. The type of image processing that depends on the imaged part is carried out according to the image processing conditions set according to the imaged part.

The image analysis unit 47 analyses the dynamic images acquired by carrying out dynamic imaging of the chest part over a plurality of time phases, and calculates the estimated ventilation volume at the different time phases. The concrete method of calculation is explained later.

The image server 5 is provided with a large capacity memory in which it stores and manages the X-ray images that have been subjected to image processing by the calculation device 4. The X-ray images stored in the image server 5 are provided for diagnosis by distributing based on the requests from the diagnosis console 3.

[Operation of the Dynamic Image Processing System 100]

Next, the operations in the above dynamic image processing system 100 are explained.

Imaging Operation:

Firstly, the flow of imaging in the dynamic image processing system 100 is explained.

Figure 3:
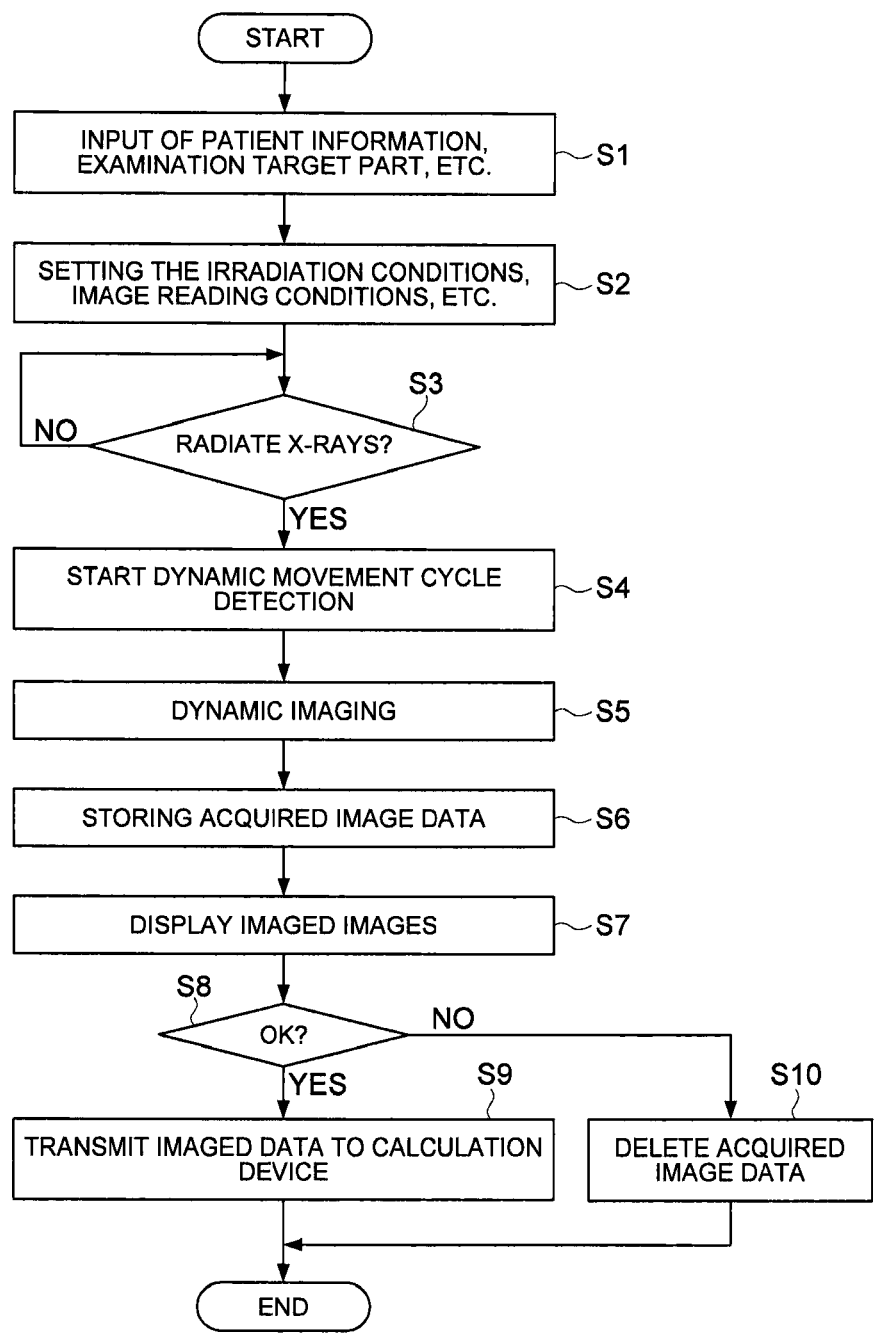
FIG. 3 is a flow chart showing the imaging control processing executed by the control unit of the imaging console shown in FIG. 1.

FIG. 3 shows the imaging flow executed in the imaging device 1 and the imaging console 2.

To begin with, the operation unit 23 of the imaging console 2 is operated by the imaging technician, and the operations of inputting the imaging target (imaging target body M) patient information, selection of the examination target part or imaging orientation, etc., are made (Step S1).

Next, from the control unit 21 of the imaging console 2, not only the irradiation conditions corresponding to the selected examination target part are read out and set in the irradiation control device 12, but also, the image reading conditions corresponding to the selected examination target part are read out from the storage unit 22 and set in the read control device 14 (Step S2).

Next, an irradiation instruction by operating the operation unit 23 is awaited, and when an irradiation instruction is input from the operation unit 23 (YES in Step S3), a cycle detection start instruction is output from the control unit 21 to the cycle detection device 16, and not only the detection of the cycles of the dynamic movements of the examination target part of the body under examination M is started by the cycle detection sensor 15 and the cycle detection device 16 (Step S4), but also the imaging start instruction is output to the irradiation control device 12 and the read control device 14 for imaging the dynamic image by the imaging device 1 (Step S5). In other words, radiation is emitted by the radiation source 11 at the pulse interval set in the irradiation control device 12, and image data is acquired by the radiation detection device 13. When a dynamic movement cycle (for example, once respiration cycle of the lungs) set in advance is detected by the cycle detection device 16, an imaging end instruction is output by the control unit 21 to the irradiation control device 12 and the read control device 14, and the imaging operation is ended.

The image data acquired by imaging is input successively to the imaging console, and, by the control unit 21, not only the image data is stored in the storage unit 22 while establishing correspondence with a number indicting the order of imaging (Step S6), but also the image is displayed in the display unit 24 (Step S7). The imaging technician confirms the positioning, etc., from the sequence of dynamic images displayed, and judges whether images suitable for diagnosis have been obtained by imaging (imaging OK) or imaging again is necessary (imaging NG). Next, the judgment result is input by operating the operation unit 23.

When the judgment result of imaging OK is input by making a prescribed operation in the operation unit 23 (YES in Step S8), by the control unit 21, each of the sequence of image data acquired by dynamic imaging (the image data of dynamic images) is added information such as that of an identification number for identifying the dynamic image, the patient information, examination target part, irradiation conditions, image reading conditions, number indicating the imaging sequence, etc. (for example, written in the header area of the DICOM format image data), and is transmitted to the calculation device 4 via the communication unit 25 (Step S9). After that, this processing is ended. On the other hand, when the judgment result of imaging NG is input by making a prescribed operation in the operation unit 23 (NO in Step S8), by the control unit 21, the sequence of image data stored in the storage unit 22 is deleted (Step S10), and this processing is ended.

Operation of the Calculation Device 4:

Next, the operations in the calculation device are explained.

Figure 4:
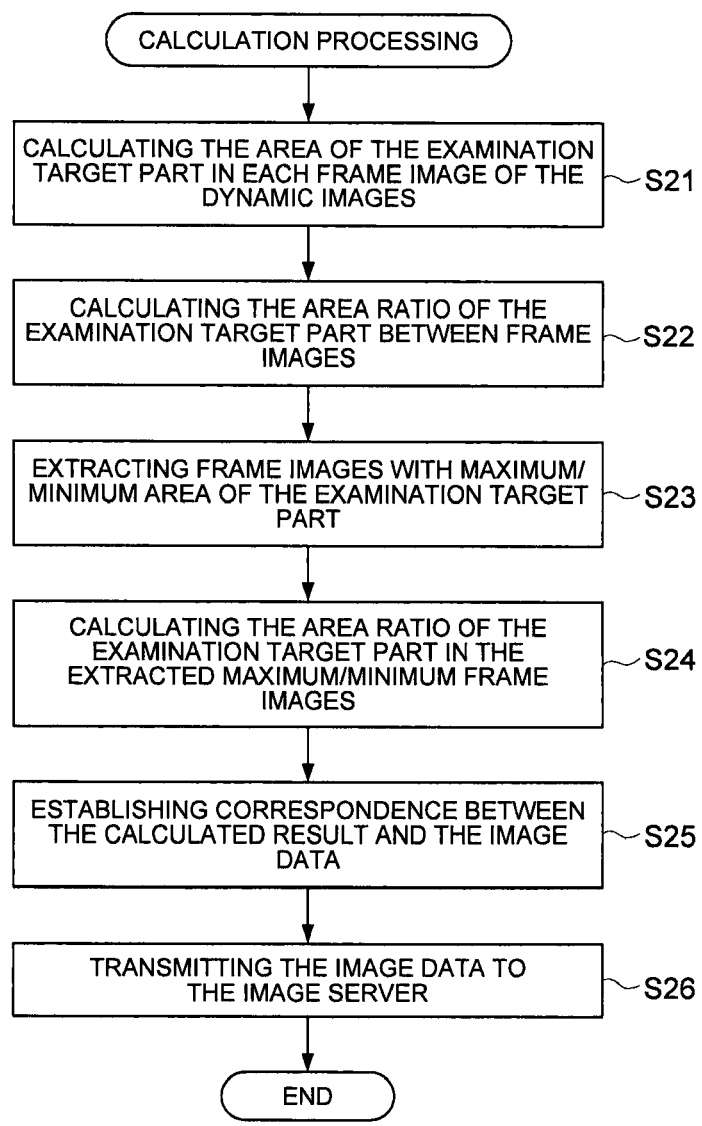
FIG. 4 is a flow chart showing the calculation processing executed by the control unit of the calculation device shown in FIG. 1.

In the calculation device 4, when a sequence of image data of dynamic images are received via the communication unit 45 from the imaging console 2, the calculation processings shown in FIG. 4 are carried out by the cooperation between the control unit 48 and the calculation processing program stored in the storage unit 51.

In the calculation processing, to begin with, for each frame image of the sequence of the received image data of dynamic images, the examination target part is recognized, and its area is calculated (Step S21). The recognition of the image area of the examination target part is carried out by programs for each of the examination target parts that have been stored in advance.

For example, when the examination target parts are the lungs (ventilation), the region of the pulmonary field is recognized by the following processing, and the area is calculated.

In the pulmonary field region, since the amount of X-ray transmission is high, the signal value becomes high compared to its neighboring regions. Therefore, for example, firstly, a density histogram is prepared from the signal values of each of the pixels, and the threshold value is obtained by the discriminant analysis method, etc. Next, a region with signal values higher than the obtained threshold value is extracted as the candidate for the pulmonary field region. Next, edge detection is carried out near the border of the candidate region, and the points where the edge becomes a maximum in the small zones near the border are extracted successively along the border. Next, the extracted edge points are approximated by a polynomial expression thereby obtaining the boundary line of the pulmonary field, the number of pixels inside the obtained boundary line is counted, and the area is calculated based on the counted number of pixels. The result of calculation is stored temporarily in the RAM of the control unit 48 while establishing correspondence with a number indicating the imaging sequence of each frame image.

Further, for example, if the examination target part is the heart, the heart region is recognized by the following processing, and the area is calculated.

To begin with, the pulmonary field region is recognized, and the search region is restricted in a rectangular region touching the outer periphery of the pulmonary field region. Next, a density histogram is prepared from the signal values of each of the pixels in the search region, a threshold value is obtained by the discriminant analysis method, etc., a region with signal values lower than the threshold value is extracted as the candidate for the heart region. Next, edge detection is carried out within the candidate region, and edge points larger than a prescribed value are extracted. Next, for an edge image constituted by the edge points and the boundary line of the candidate region, template matching is done with a template having the shape of a heart, and the template region at the position where the correlation function value becomes highest is recognized as the heart region. When this heart region is recognized, the number of pixels inside the recognized region is counted, and its area is calculated based on the counted number of pixels. The result of calculation is stored temporarily in the RAM of the control unit 48 while establishing correspondence with a number indicating the imaging sequence of each frame image.

Next, the area ratios are calculated respectively of the image regions of the examination target part between neighboring frame images in the imaging sequence (Step S22). In concrete terms, for each frame image, the area ratio is calculated of the image region of the examination target part in that frame image with respect to the image region of the examination target part in the immediately previous frame image. The result of calculation is stored temporarily in the RAM of the control unit 48 while establishing correspondence with a number indicating the imaging sequence of each frame image.

Next, from the sequence of frame images, the frame image with the maximum area of the image region of the examination target part (the maximum image) and the frame image with the minimum area of the image region of the examination target part (the minimum image) are extracted (Step S23), and the area ratio is calculated of the image regions of the examination target part in the extracted maximum image and the minimum image (Step S24). The result of calculation is stored temporarily in the RAM of the control unit 48 while establishing correspondence with a number indicating the imaging sequence of the maximum image and the minimum image.

When the calculations of Step S21 to S24 are completed, relationship is established between the calculation results stored in the RAM and the image data of the corresponding frame image based on numbers indicating the imaging sequence and added to the image data (Step S25). For the maximum image and the minimum image, a flag indicating the maximum image and a flag indicating the minimum image are also added. Next, the sequence of image data that is input is transmitted via the communication unit 45 to the image server 5 (Step S26), and this processing is ended.

In the image server 5, when the sequence of image data of the dynamic images is received from the calculation device 4, the received sequence of image data is stored in the storage device.

Operation of the Diagnosis Console 3:

Next, the operations in the diagnosis console 3 are explained.

Figure 5:
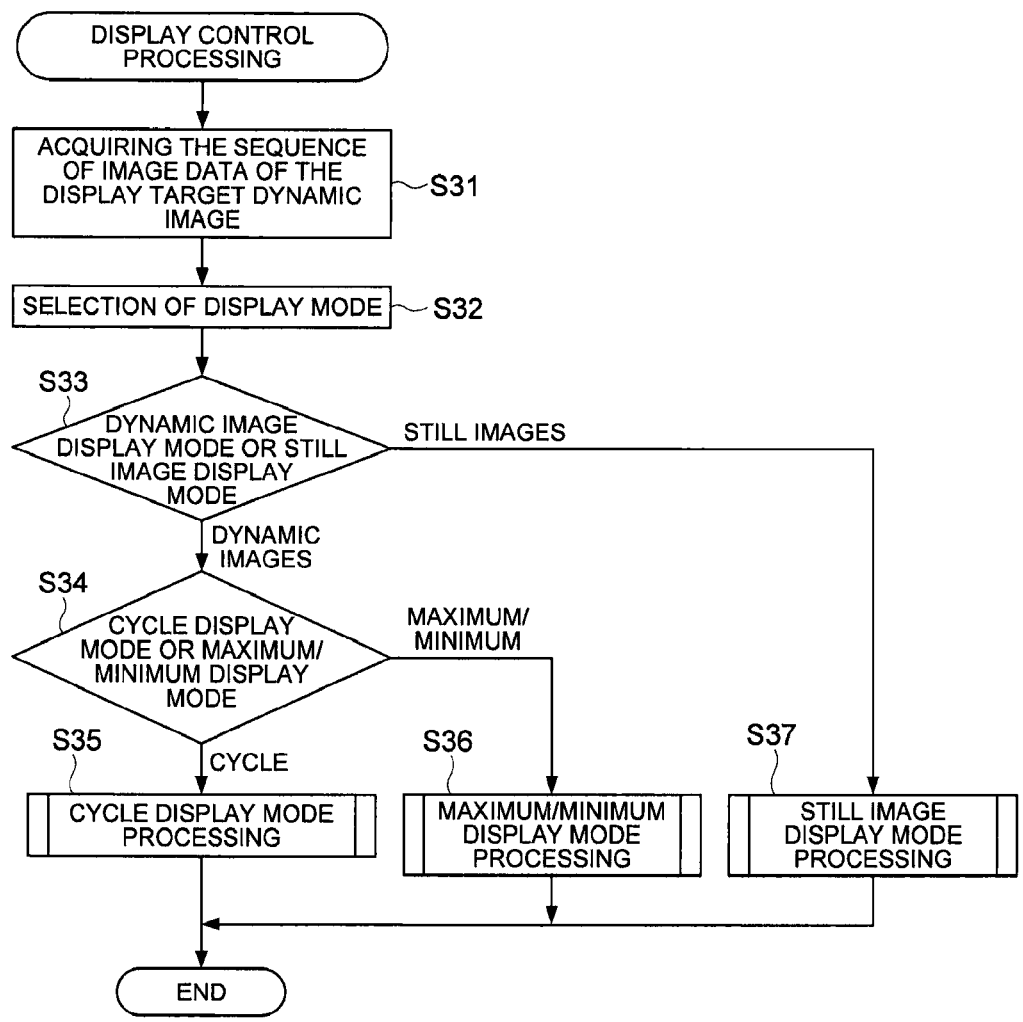
FIG. 5 is a flow chart showing the display control processing executed by the control unit of the diagnosis console shown in FIG. 1.

In the diagnosis console 3, when the identification ID of the dynamic image which is the target of display is input from the operation unit 33 and image display is instructed, due to the coordination between the control unit 31 and the display control program stored in the storage unit 32, the display control processing shown in FIG. 5 is executed. The display control unit is realized by the execution of this processing.

To begin with, via the communication unit 35, an acquisition request is transmitted to the image server 5 requesting for the sequence of image data (frame images) having the identification ID that has been input, and the sequence of image data of the display target dynamic images is acquired from the image server 5 (Step S31).

Next, a display mode selection screen not shown in the figure is displayed in the display unit 34, and the selection of the display mode is received from the operation unit 33 (Step S32). In the display mode selection screen, it is possible to select using the operation unit 33 the display mode to be used for displaying the acquired dynamic images from the modes of the "dynamic image display mode" and the "still image display mode". The dynamic image display mode is a mode in which moving image display is made in the display screen of the display unit 34 by successively switching the display of the acquired sequence of frame images of the dynamic image in the imaging sequence. The still image display mode is a mode in which, in the display screen of the display unit 34, still image display is made by arranging in the imaging sequence the acquired sequence of frame images of the dynamic image. For the dynamic image display mode, in addition, it is possible to select the detailed modes of the "cycle display mode" or the "maximum/minimum display mode".

When the "dynamic image display mode" is selected as the display mode of the dynamic image from the operation unit 33 (Dynamic in Step S33), and if the cycle display mode is selected as the detailed mode (Cycle in Step S34), the cycle display mode processing (see FIG. 6) is executed (Step S35), and this processing is ended.

When the "dynamic image display mode" is selected as the display mode of the dynamic image from the operation unit 33 (Dynamic in Step S33), and if the maximum/minimum display mode is selected as the detailed mode (Maximum/minimum in Step S34), the maximum/minimum display mode processing (see FIG. 7) is executed (Step S36), and this processing is ended.

On the other hand, if the "still image mode" is selected as the display mode of the dynamic image from the operation unit 33 (Still image in Step S33), the still image display processing (see FIG. 8) is executed (Step S37), and this processing is ended.

In the following, referring to FIG. 6 to FIG. 10, the cycle display mode processing, the maximum/minimum display mode processing, and the still image display mode processing are explained.

Figure 6:
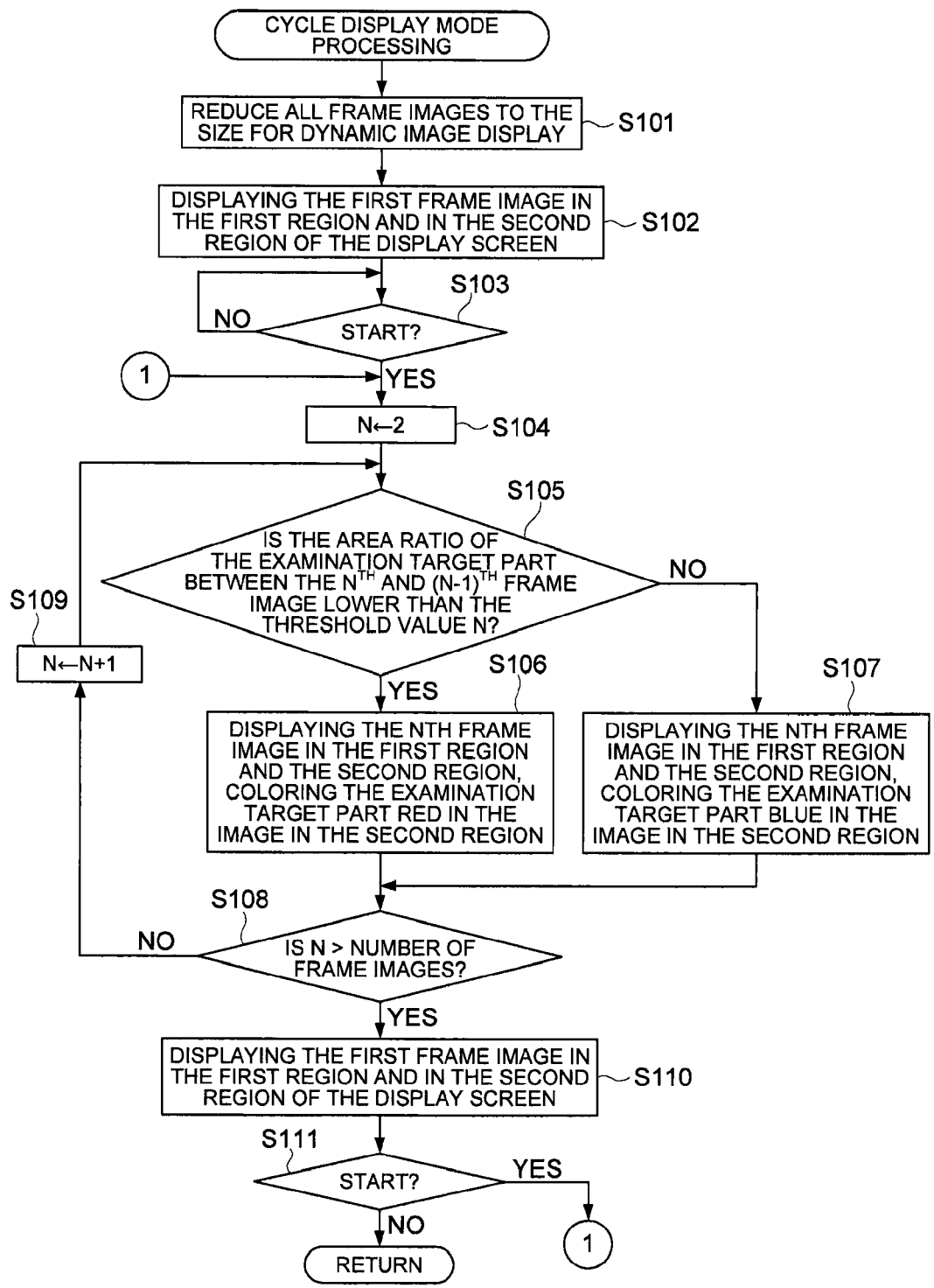
FIG. 6 is a flow chart showing the cycle display mode processing executed by the control unit of the diagnosis console shown in FIG. 1.

To begin with, referring to FIG. 6, the cycle display mode processing executed in the Step S35 of FIG. 5 is explained. This processing is realized by software processing due to the coordination between the control unit 31 and the cycle display mode processing program stored in the storage unit 32.

To begin with, reduction interpolation processing such as decimating processing, etc., is carried out for all the acquired frame images, and reduced images are prepared with a predetermined size for dynamic image display (size corresponding to the first region 341a and the second region 341b in the dynamic image display screen 341 (see FIG. 9)) (Step S101). Next, a dynamic image display screen 341 is displayed in which the first frame in the imaging sequence is displayed in the first region 341a and the second region 341b in the display screen of the display unit 34 (Step S102).

Figure 9:
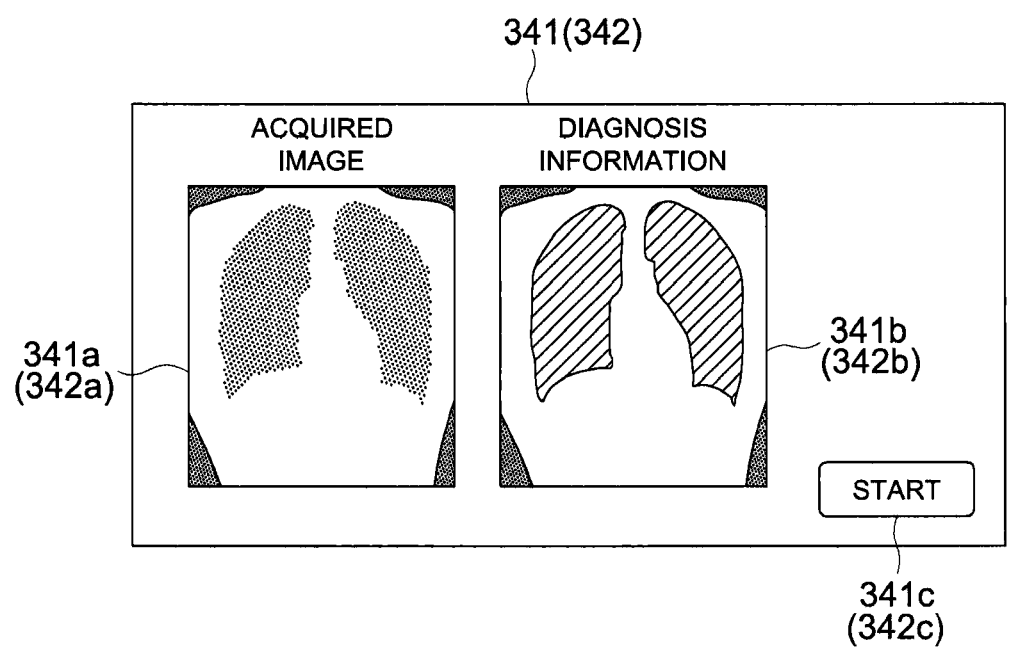
FIG. 9 is a diagram showing an example of the dynamic image display screen displayed in the dynamic image display mode.

FIG. 9 shows an example of the dynamic image display screen 341. As shown in FIG. 9, the dynamic image display screen 341 has a first region 341a and a second region 341b. The first region 341a is the area for making a moving image display by successively switching in the imaged sequence the sequence of frame images of the acquired dynamic image. The second region 341b is the area for displaying, at the same time as in the first region 341a, by successively switching in the imaged sequence the sequence of frame images of the acquired dynamic image, and for displaying the frame image by coloring it in a color according to the area ratio of the image region of the examination target part between the frame image that is currently being displayed in the first region 341a and its immediately previous frame image (the immediately previous image in the imaging sequence) calculated by the calculation device 4. In other words, the frame image being displayed is displayed after modifying (coloring) a part of it. Further, the dynamic image display screen 341 has a start button 341c, and when the start button is pressed in the operation unit 33, the moving image display of the dynamic image is started.

The pressing of the start button 341c in the operation unit 33 is waited for, and when the start button 341c is pressed (YES in Step S103), the value 2 is set in the counter N (Step S104), a judgment is made as to whether or not the area ratio of the image region of the examination target part in the $N^{th}$ frame image in the imaging sequence with respect to the $(N-1)^{th}$ frame image calculated by the calculation device 4 falls below a threshold value N determined in advance (This is taken as the threshold value N. The threshold value N varies depending on the counter N.) (Step S105). When it is judged that the area ratio of the image region of the examination target part in the $N^{th}$ frame image in the imaging sequence with respect to the $(N-1)^{th}$ frame image calculated by the calculation device 4 is below the threshold value N determined in advance (YES in Step S105), the frame image with the imaging sequence number of N is displayed in the first region 341a and in the second region 341b, the region of the examination target part of the frame image displayed in the second region 341b is recognized and is displayed after being colored red (Step S106). When the area ratio of the image region of the examination target part in the $N^{th}$ frame image in the imaging sequence with respect to the $(N-1)^{th}$ frame image calculated by the calculation device 4 is judged to be exceeding the threshold value N determined in advance (NO in Step S105), the frame image with the imaging sequence number of N is displayed in the first region 341a and in the second region 341b, the region of the examination target part of the frame image displayed in the second region 341b is recognized and displayed after being colored blue (Step S107).

In general, from the structure of the human body, if the dynamic image of a certain examination target part of a healthy human is imaged using an imaging apparatus 1 with the same specifications, and under fixed conditions (for example, age, height, weight, sex, imaging state (body posture (standing/supine position)), imaging direction (PA/AP), and pulse rate), it is known that the area ratio calculated of the image region of the examination target part between neighboring frame images in the imaging sequence is within a prescribed range for each frame image imaged at the same timing (phase of the dynamic cycle). Therefore, when the area ratio calculated of the image region of the examination target part between neighboring frame images in the imaging sequence falls below a fixed value determined in advance for each imaging timing of the frame image, it is possible to judge that the movement of the examination target part is not sufficient compared to a healthy body and that it is not functioning sufficiently. For example, when the examination target part is the ventilation of the lungs, the area ratio of the pulmonary field between neighboring frame images is a feature quantity indicating the ventilation rate of the lungs, and if the area ratio is lower than a fixed value determined in advance, it is possible to recognize that the ventilation rate is not sufficient.

Here, in the cycle display mode processing, if the area ratio calculated of the image region of the examination target part between neighboring frame images in the imaging sequence falls below the threshold value N, by displaying the image region of the examination target part after coloring it red, the information that the movement of the examination target part is not normal is provided to the doctor in an easy to grasp form. In addition, if the area ratio calculated of the image region of the examination target part between neighboring frame images in the imaging sequence exceeds the threshold value N, by displaying the image region of the examination target part after coloring it blue, the information that the movement of the examination target part is normal is provided to the doctor in an easy to grasp form.

In concrete terms, as shown in FIG. 9, not only the dynamic image is displayed in the first region 341a and the dynamic image is displayed in the second region 341b, but also, in the dynamic image displayed in the second region 341b, the examination target part is displayed in red color if the area ratio of the examination target part (the pulmonary field in FIG. 9) between the frame image being currently displayed and its immediately previous frame image falls below the threshold value N, and it is displayed in blue if the area ratio exceeds the threshold value N. In this manner, by displaying the dynamic image in the cycle display mode, the doctor, while observing the acquired image in the first region 341a, can grasp in an easy manner, in the second region 341b, whether or not the examination target part is functioning sufficiently in the displayed frame image.

Further, since the amount of change in the image area due to movement of the examination target part varies according to the conditions such as the age, height, weight, sex, imaging state (body posture (standing/supine position)), imaging direction (PA/AP), and pulse rate, etc., for each examination target part, the threshold value N is calculated and stored in advance for each of these conditions, and the threshold value N is changed according to the examination target part, age, height, weight, sex, imaging conditions, etc. of the imaged body M during imaging.

Returning to FIG. 6, in Step S108, a judgment is made as to whether or not the counter N is greater than the number of frame images, and if it is judged that N is not greater than the number of frame images (NO in Step S108), the counter N is incremented by 1 (Step S109), and the processing returns to Step S105. If it is judged that N is greater than the number of frame images (YES in Step S108), the first frame image in the imaging sequence is displayed in the first region 341a and the second region 341b of the dynamic image display screen 341 (Step S109). When the start button 341c is pressed in the operation unit 33 (YES in Step S111), the processing returns to Step S104, and the dynamic image is displayed again. If the start button is not pressed (NO in Step S111), the cycle display mode processing is ended.

Figure 7:
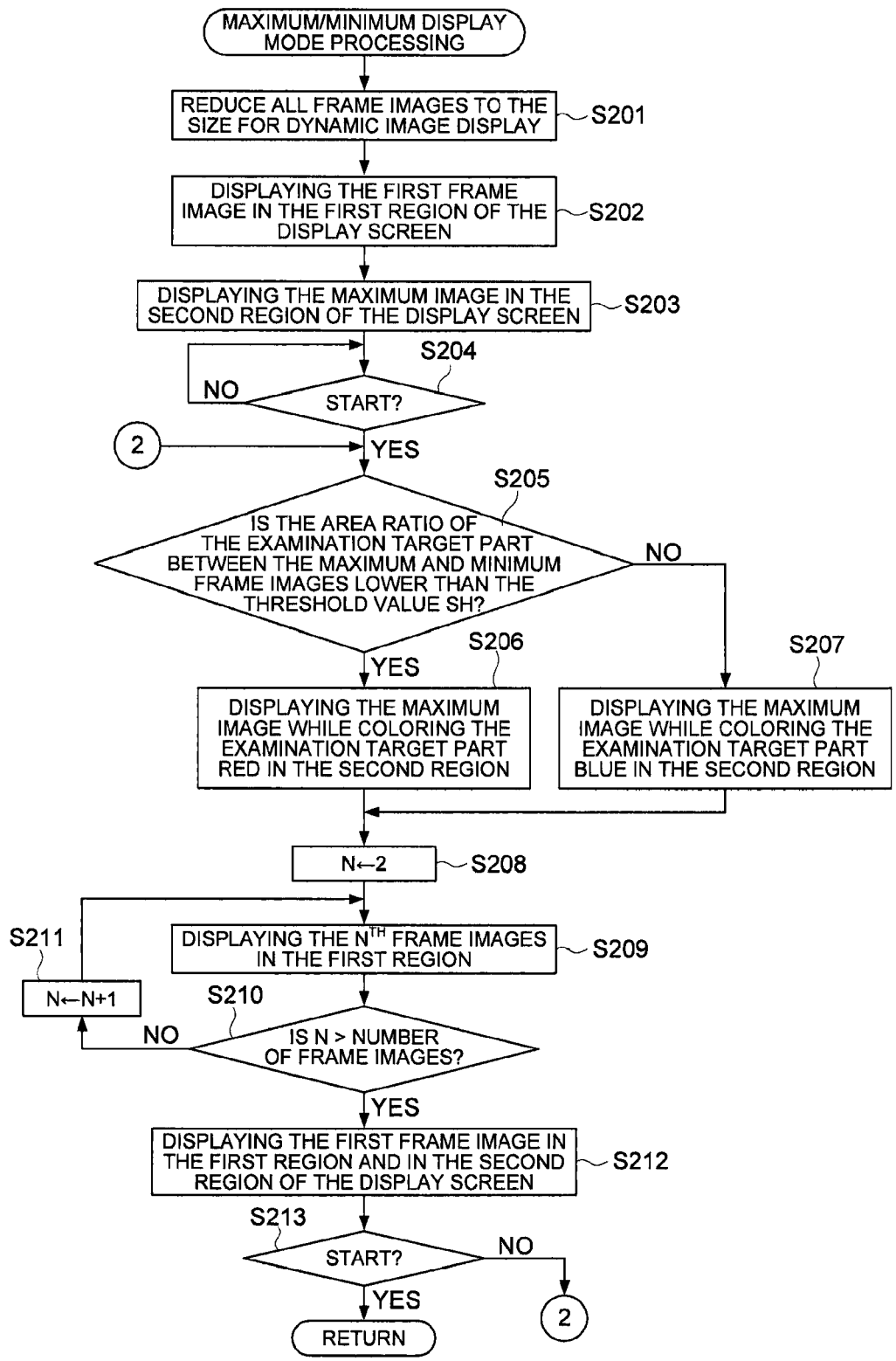
FIG. 7 is a flow chart showing the maximum/minimum display mode processing executed by the control unit of the diagnosis console shown in FIG. 1.

Next, referring to FIG. 7, the maximum/minimum display mode processing executed in Step S36 of FIG. 5 is explained. This processing is realized by software processing due to the coordination between the control unit 31 and the maximum/minimum display mode processing program stored in the storage unit 32.

To begin with, reduction interpolation processing such as decimating processing, etc., is carried out for all the acquired frame images, and reduced images are prepared with a predetermined size for dynamic image display (size corresponding to the first region 342a and the second region 342b in the dynamic image display screen 342 (see FIG. 9)) (Step S201). Next, a dynamic image display screen 342 is displayed in which the first frame in the imaging sequence is displayed in the first region 341a (Step S202), and the maximum image is displayed in the second region 341b (Step S203).

FIG. 9 shows an example of the dynamic image display screen 342. As shown in FIG. 9, the dynamic image display screen 342 has a first region 342a and a second region 342b. The first region 342a is the area for making a moving image display by successively switching in the imaged sequence the sequence of frame images of the acquired dynamic image. The second region 342b is the area for displaying, among the sequence of frame images, the maximum image in which the area of the examination target part is a maximum, and is the region for displaying the frame image by coloring it in a color according to the area ratio of the image region of the examination target part between the maximum frame image and the minimum frame image calculated by the calculation device 4. Further, the dynamic image display screen 342 has a start button 342c, and when the start button 342c is pressed by the operation unit 33, the moving image display of the dynamic image in the first region 342a and the colored image display in the second region 342b are started.

Next, the pressing of the start button 342c in the operation unit 33 is waited for, and when the start button 342c is pressed (YES in Step S204), a judgment is made as to whether or not the area ratio of the image region of the examination target part between the maximum image and the minimum image calculated by the calculation device 4 falls below a threshold value N determined in advance (This is taken as the threshold value SH.) (Step S205). When it is judged that the area ratio of the image region of the examination target part between the maximum image and the minimum image calculated by the calculation device 4 is below the threshold value SH determined in advance (YES in Step S205), the region of the examination target part in the maximum frame image displayed in the second region 342b is recognized and is displayed after being colored red (Step S206). When the area ratio of the image region of the examination target part between the maximum image and the minimum image calculated by the calculation device 4 is judged to be exceeding the threshold value SH determined in advance (NO in Step S205), the region of the examination target part in the maximum frame image displayed in the second region 342b is recognized and is displayed after being colored blue (Step S207).

In general, from the structure of the human body, if the dynamic image (for more than one cycle) of a certain examination target part of a healthy human is imaged using an imaging apparatus 1 with the same specifications, and under fixed conditions (for example, age, height, weight, sex, imaging state (body posture (standing/supine position)), and imaging direction (PA/AP)), it is known that the area ratio calculated of the image region of the examination target part between the maximum image in which the area of the examination target part becomes a maximum and the minimum image in which the area of the examination target part becomes a minimum is within a prescribed range. Therefore, when the area ratio calculated of the image region of the examination target part between the maximum image and the minimum image falls below a fixed value determined in advance, it is possible to judge that the movement of the examination target part is not sufficient compared to a healthy body and that it is not functioning sufficiently. For example, when the examination target part is the ventilation of the lungs, the area ratio of the pulmonary field between the maximum image and the minimum image indicates the ventilation rate of the lungs, and if the area ratio is lower than a fixed value determined in advance, it is possible to recognize that the ventilation rate is not sufficient.

In view of this, in the maximum/minimum display mode processing, if the area ratio calculated of the image region of the examination target part between the maximum image and the minimum image falls below the threshold value SH, by displaying the image region of the examination target part after coloring it red, the information that the movement of the examination target part is not normal is provided to the doctor in an easy to grasp form. In addition, if the area ratio calculated of the image region of the examination target part between the maximum image and the minimum image exceeds the threshold value SH, by displaying the image region of the examination target part after coloring it blue, the information that the movement of the examination target part is normal is provided to the doctor in an easy to grasp form.

In concrete terms, as shown in FIG. 9, not only the dynamic image is displayed in the first region 342a, and the dynamic image is displayed in the second region 342b, but also, in the dynamic image displayed in the second region 342b, the examination target part is displayed in red color if the area ratio of the examination target part (the pulmonary field in FIG. 9) between maximum image and the minimum image falls below the threshold value SH, and it is displayed in blue if the area ratio exceeds the threshold value SH. In this manner, by displaying the dynamic image in the maximum/minimum display mode, the doctor, while observing the acquired image in the first region 342a, can grasp in an easy manner, in the second region 342b, whether or not the examination target part is functioning sufficiently in the displayed frame image.

Further, since the amount of change in the image area due to movement of the examination target part varies according to the conditions such as the age, height, weight, sex, imaging state (body posture (standing/supine position)), imaging direction (PA/AP), etc., for each examination target part, the threshold value SH is calculated and stored in advance for each of these conditions, and the threshold value SH is changed according to the examination target part, age, height, weight, sex, imaging conditions, etc. of the imaged body M during imaging.

Returning to FIG. 7, in Step S208, the value 2 is set in the counter N (Step S208), and the $N^{th}$ frame image in the imaging sequence is displayed in the first region 342a (Step S209). At this time, the display in the second region 342b does not change. Next, a judgment is made as to whether or not the counter N is greater than the number of frame images, and if it is judged that N is not greater than the number of frame images (NO in Step S210), the counter N is incremented by 1 (Step S211), and the processing returns to Step S209. If it is judged that N is greater than the number of frame images (YES in Step S210), the first frame image in the imaging sequence is displayed in the first region 342a and the maximum image is displayed in the second region 342b of the dynamic image display screen 342 (Step S212). When the start button 342c is pressed by the operation unit 33 (YES in Step S213), the processing returns to Step S205, and the dynamic image is displayed again. If the start button is not pressed (NO in Step S213), the maximum/minimum display mode processing is ended.

Further, in the FIG. 7, although the explanations were given taking that the maximum image is displayed in the second region 342b, it is also possible to display the minimum image.

Figure 8:
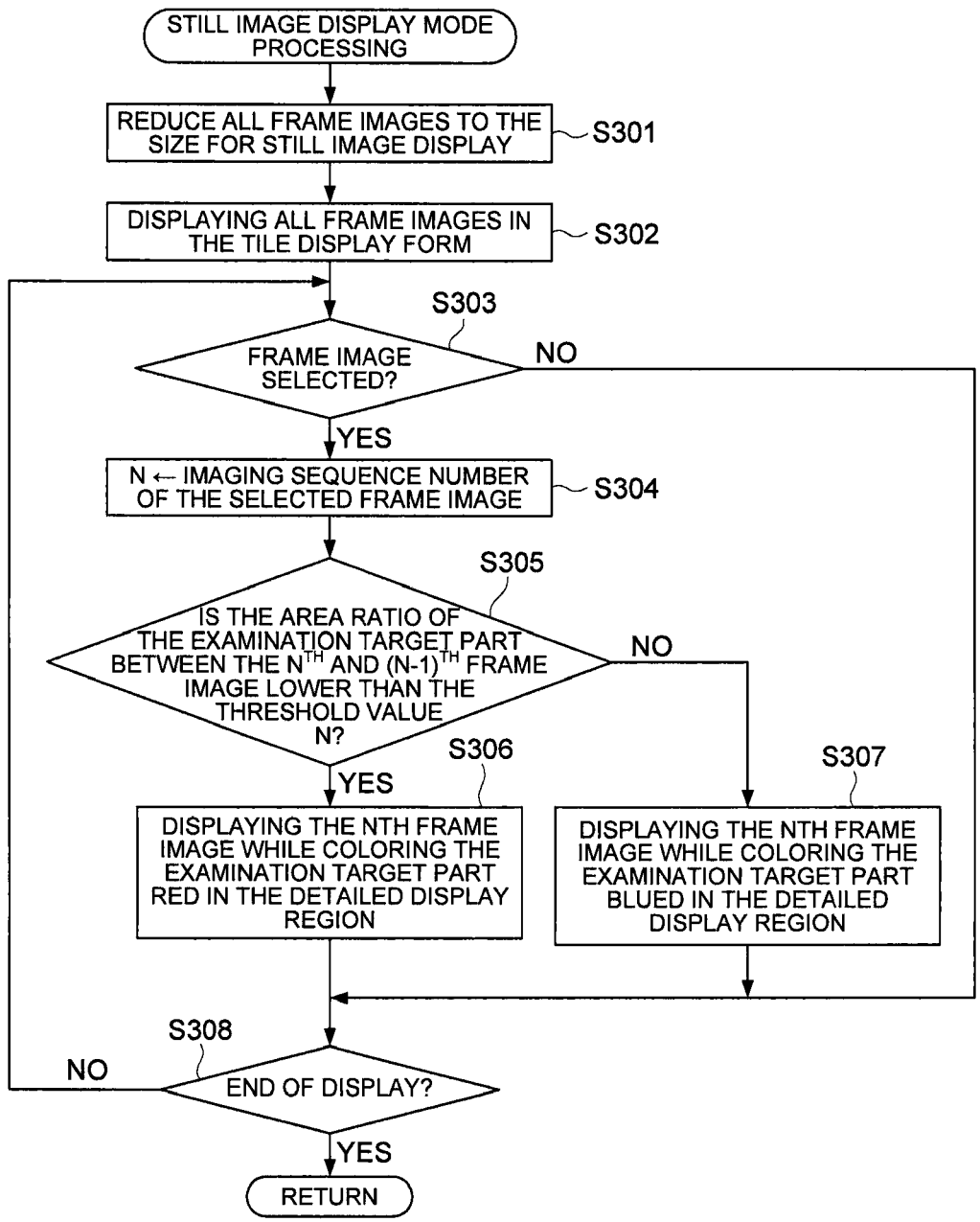
FIG. 8 is a flow chart showing the still images display mode processing executed by the control unit of the diagnosis console shown in FIG. 1.

Next, referring to FIG. 8, the still image display mode processing executed in Step S37 of FIG. 5 is explained. This processing is realized by software processing due to the coordination between the control unit 31 and the still image display mode processing program stored in the storage unit 32.

To begin with, reduction interpolation processing such as decimating processing, etc., is carried out for all the acquired frame images, and reduced images are prepared with a predetermined size for still image display (size corresponding to the thumbnail region 343a and the detailed display region 343b in the still image display screen 343 (see FIG. 10)) (Step S301). Next, a still image display screen 343 is displayed in which the thumbnail images of the sequence of frame images are displayed by being arranged in the form of a tile display in the thumbnail region 343a (Step S302).

Figure 10:
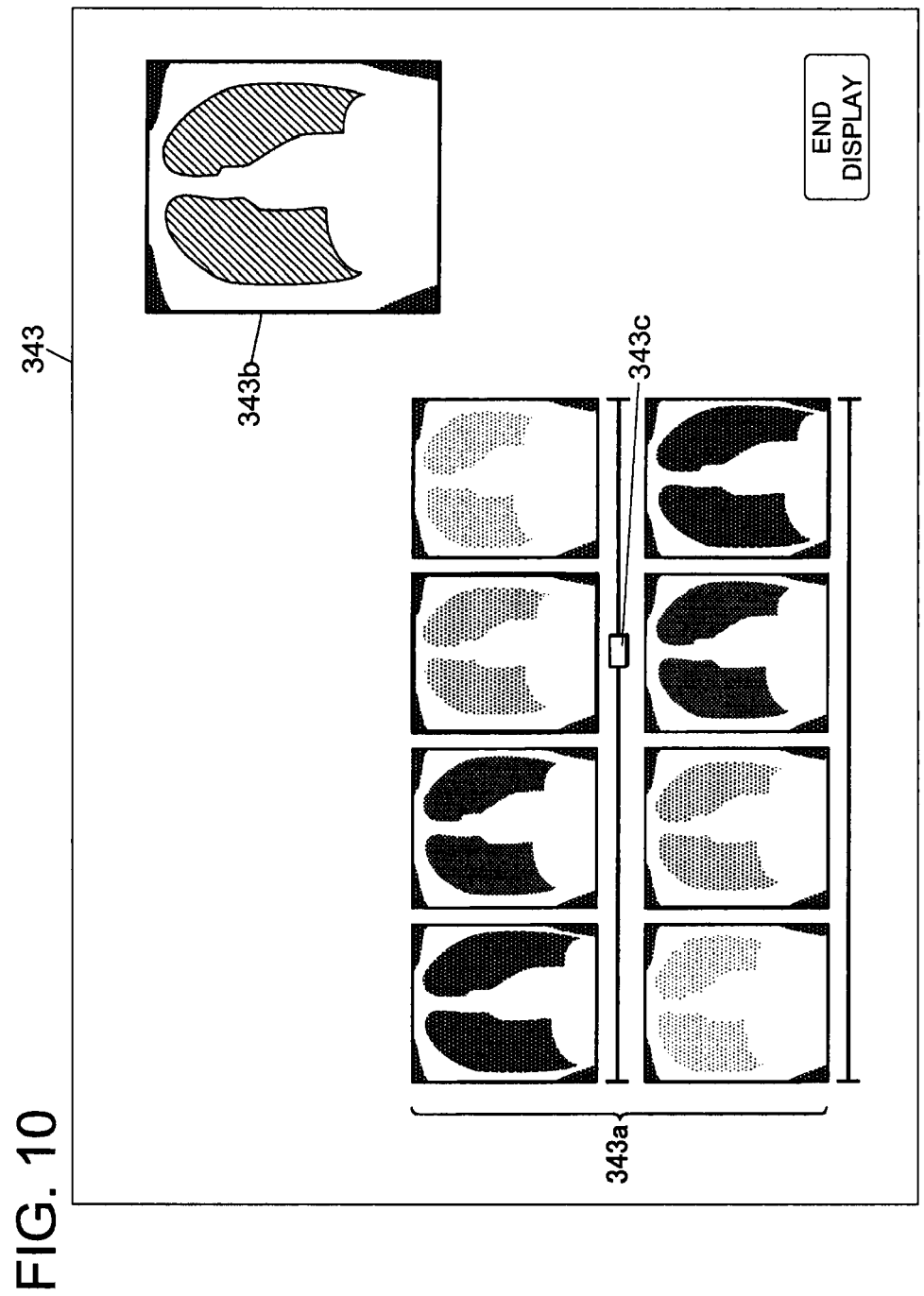
FIG. 10 is a diagram showing an example of the still image display screen displayed in the still image display mode.

FIG. 10 shows an example of the still image display screen 343. As shown in FIG. 10, the still image display screen 343 has a thumbnail region 343a in which is made a tile display of the sequence of frame images and a detailed display region 343b in which a frame image specified by an operation from the operation unit 33 from among the frame images displayed in the thumbnail region 343a is displayed with a size larger than the thumbnail image. In the bottom part of the thumbnail region 343a is displayed a slide bar 343c, and by moving the position of the slide bar below a desired frame image via an the operation in the operation unit 33, it is possible to specify the frame image which is displayed in the detailed display region 343b according to the position of the slide bar. Further, the frame image displayed in the detailed display region 343b can also be made to be specified by a mouse that specifies the image in the thumbnail region 343a.

When a frame image is specified via the operation unit 33 from the still image display screen 343 (YES in Step S303), a number indicating the imaging sequence of the specified frame image is set in the counter N (Step S304), a judgment is made as to whether or not the area ratio of the image region of the examination target part in the $N^{th}$ frame image in the imaging sequence with respect to the $(N-1)^{th}$ frame image calculated by the calculation device 4 falls below a threshold value determined in advance (This is taken as the threshold value N. The threshold value N varies depending on the counter N.) (Step S305). When it is judged that the area ratio of the image region of the examination target part in the $N^{th}$ frame image in the imaging sequence with respect to the $(N-1)^{th}$ frame image calculated by the calculation device 4 is below the threshold value N determined in advance (YES in Step S305), the frame image with the imaging sequence number of N is displayed in the detailed display region 343b, the region of the examination target part of the displayed frame image is recognized and is displayed after being colored red (Step S306), and the processing transits to Step S308. On the other hand, when the area ratio of the image region of the examination target part in the $N^{th}$ frame image in the imaging sequence with respect to the $(N-1)^{th}$ frame image calculated by the calculation device 4 is judged to be exceeding the threshold value N determined in advance (NO in Step S305), the frame image with the imaging sequence number of N is displayed in the detailed display region 343b, the region of the examination target part of the displayed frame image is recognized and is displayed after being colored blue (Step S307).

In general, from the structure of the human body, if the dynamic image of a certain examination target part of a healthy human is imaged using an imaging apparatus 1 with the same specifications, and under fixed conditions (for example, age, height, weight, sex, imaging state (body posture (standing/supine position)), imaging direction (PA/AP), and pulse rate), it is known that the area ratio calculated of the image region of the examination target part between neighboring frame images in the imaging sequence is within a prescribed range for each frame image imaged at the same timing (phase of the dynamic cycle). Therefore, when the area ratio calculated of the image region of the examination target part between neighboring frame images in the imaging sequence falls below a fixed value determined in advance for each imaging timing of the frame image, it is possible to judge that the movement of the examination target part is not sufficient compared to a healthy body and that it is not functioning sufficiently. For example, when the examination target part is the ventilation of the lungs, the area ratio of the pulmonary field between neighboring frame images is a feature quantity indicating the ventilation rate of the lungs, and if the area ratio is lower than a fixed value determined in advance, it is possible to recognize that the ventilation rate is not sufficient.

Here, in the still image display mode processing, if the area ratio of the image region of the examination target part between neighboring frame images in the imaging sequence falls below the threshold value N, by displaying the image region of the examination target part after coloring it red, the information that the movement of the examination target part is not normal is provided to the doctor in an easy to grasp form. In addition, if the area ratio calculated of the image region of the examination target part between neighboring frame images in the imaging sequence exceeds the threshold value N, by displaying the image region of the examination target part after coloring it blue, the information that the movement of the examination target part is normal is provided to the doctor in an easy to grasp form.

In concrete terms, as shown in FIG. 10, when one frame image is specified from among the thumbnail images displayed in the thumbnail region 343a, the selected frame image is displayed in the detailed display region 343b with a size larger than the thumbnail image, and also, in the frame image displayed in the detailed display region 343b, the examination target part is displayed in red color if the area ratio of the examination target part (the pulmonary field in FIG. 10) between the frame image being currently displayed and its immediately previous frame image falls below the threshold value N, and it is displayed in blue if the area ratio exceeds the threshold value N. In this manner, since all the frame images of the dynamic image in the still image display mode are displayed in a tile display in the thumbnail region, and the selected frame image is displayed after coloring it according to the area ratio of the examination target part between the currently displayed frame image and its immediately previous frame image, it is possible for the doctor, while observing the entire dynamic image as still images, and can grasp in an easy manner whether or not the examination target part is functioning sufficiently by selecting a frame image of interest among the displayed frame images.

Further, since the amount of change in the image area due to movement of the examination target part varies according to the conditions such as the age, height, weight, sex, imaging state (body posture (standing/supine position)), imaging direction (PA/AP), and pulse rate, etc., for each examination target part, the threshold value N is calculated and stored in advance for each of these conditions, and the threshold value N is changed according to the examination target part of the imaged body M during imaging, the age, height, weight, sex, imaging conditions, etc.

Returning to FIG. 8, in Step S308, a judgment is made as to whether or not the display end instruction was input from the operation unit 33, and if it is judged that such an instruction has not been input (NO in Step S308), the processing returns to Step S303. If it is judged that the display end instruction has been input from the operation unit 33 (YES in Step S308), this processing is ended.

As has been explained above, according to the dynamic image processing system 100, in the calculation device 4, a feature quantity of dynamic movement is extracted based on the plurality of frame images of the dynamic image imaged by the imaging device 1, and in the diagnosis console 3, not only the imaged dynamic image is displayed in the display unit 34 as a dynamic image display or as a still image display, among a plurality of frame images, at least one frame image is displayed on the display screen after coloring it in a color according to the result of calculation of the feature quantity by the calculation device 4. Therefore, since both the imaged dynamic image and an image colored according to a feature quantity extracted from that dynamic image are displayed at the same time in the display screen, it becomes possible for the doctor to grasp the feature quantity in the dynamic image while observing the imaged dynamic image, and it is possible to increase the performance of diagnosis using dynamic images.

Further, since the diagnosis console 3 has the dynamic image display mode in which a moving images display is made of the dynamic images on the display screen, and the still images display mode of displaying the images as still images arranged in the form of a tile display, and since it is possible to select the dynamic image display mode or the still image display mode from the operation unit 33, it is possible to display the dynamic images in a form which is easy for the doctor to diagnose.

Further, in the dynamic image display mode called the cycle display mode, since not only dynamic image display is made in the display screen of a plurality of frame images showing the dynamic movements, but also, since the frame image that is currently being displayed in the dynamic image is displayed in parallel with the dynamic display after being colored with a color according to the area ratio of the examination target part between that frame image and the frame image immediately previous to that in the imaging sequence, it becomes possible for the doctor to grasp easily whether or not the examination target part is functioning sufficiently at the time when the frame image being displayed was imaged.

Further, in the dynamic image display mode called the maximum/minimum display mode, since not only dynamic image display is made in the display screen of a plurality of frame images showing the dynamic movements, but also, since the maximum image or the minimum image is displayed in parallel with the dynamic display after being colored with a color according to the area ratio of the examination target part between the frame image in which the area of the image region of the examination target part is a maximum (the maximum image) and the frame image in which the area of the image region of the examination target part is a minimum (the minimum image), it becomes possible for the doctor to grasp easily whether or not the examination target part on the whole is functioning sufficiently.

Further, in the still image display mode, since not only still image display is made in the display screen of a plurality of frame images arranged in parallel in the form of a tile display and showing the dynamic movements, but also, since a frame image selected via the operation unit 33 is displayed after being colored with a color according to the area ratio of the examination target part between that frame image and the frame image immediately previous to that in the imaging sequence, it becomes possible for the doctor to grasp easily whether or not the examination target part is functioning sufficiently at the time when the frame image of interest was imaged.

Further, although the descriptions in the above preferred embodiment were of an example of a medical image management system suitable for the present invention, and the present invention is not limited to this.

For example, in the above preferred embodiment, although it was explained that the frame image is colored according to the judgment result of whether or not the feature quantity (area ratio) calculated in the calculation device 4 falls below a threshold value determined in advance, it is also possible to divide the threshold value in advance into a plurality of ranks and to display after coloring in a color according to the rank of the feature quantity calculated from the dynamic image.

Further, in the above preferred embodiment, although the diagnosing capacity was increased by displaying in the display screen both the imaged dynamic image and the colored dynamic image (frame image), it is also possible to consider the form of displaying by superimposing the color according to the feature quantity on the imaged dynamic image.

Further, for example, in the above explanations, although an example was disclosed in which an HDD or a semiconductor nonvolatile memory, etc., was used as a computer readable medium for the programs related to the present invention, it is not necessary to restrict to this example. As other computer readable media, it is possible to use a portable recordable medium such as a CD-ROM, etc. Further, a carrier wave can also be applied as the medium for providing via communication lines the data of the programs related to the present invention.

Apart from this, even regarding the detailed configurations and detailed operations of the different devices constituting the dynamic image processing system 100, it is possible to make appropriate modifications without deviating from the scope and intent of the present invention.

Estimated Ventilation Quantity Calculation and Display Processing:

If a dynamic image processing system 100 according to the present preferred embodiment is used, it is possible to carry out dynamic imaging of the chest part, to analyze the images using the acquired different frame images at a plurality of time phases, to calculate the estimated ventilation quantities at the different time phases, and to display them (estimated ventilation quantity calculation and display processing). The operations of the estimated ventilation quantity calculation and display processing are explained below.

Figure 11:
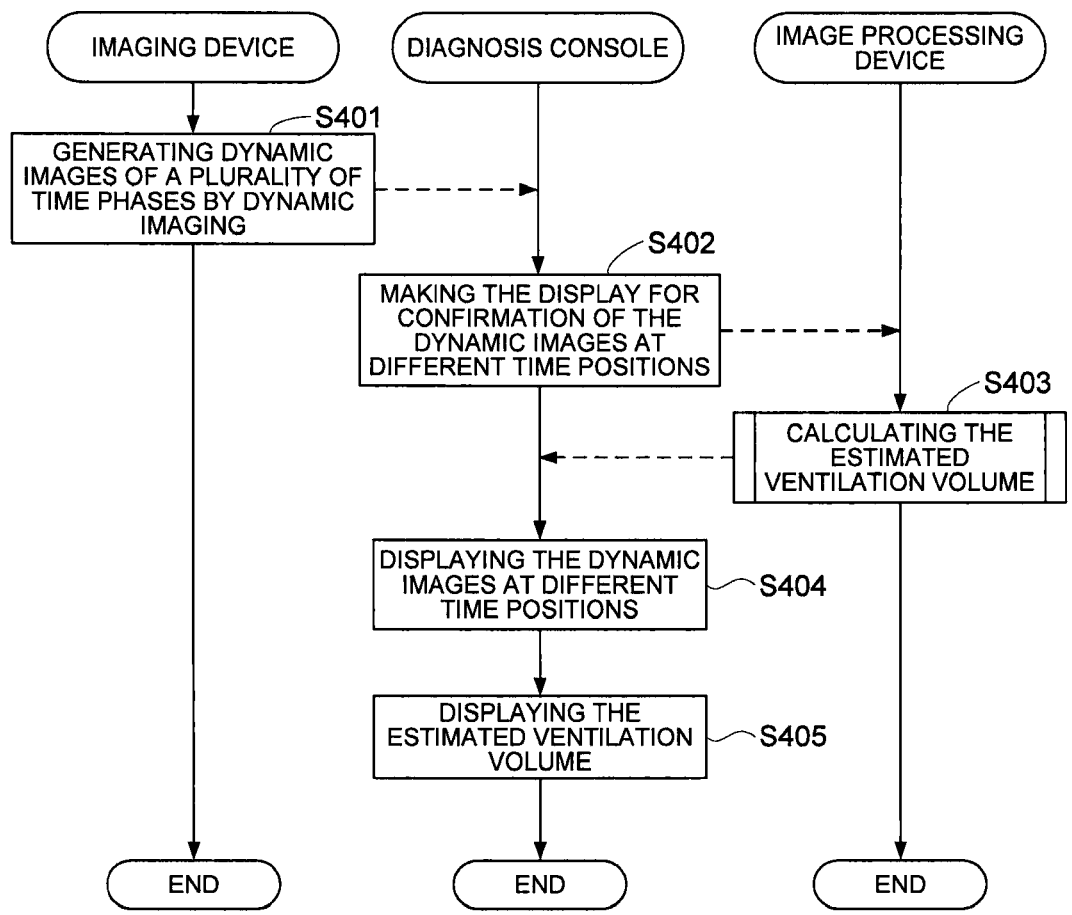
FIG. 11 is a diagram showing the flow of processing in the dynamic image processing system.

FIG. 11 is a flow chart showing the flow of processing in the imaging device 1, the diagnosis console 3, and the calculation device 4 which function mainly at that time.

As shown in FIG. 11, to begin with, dynamic imaging is carried out in the imaging device 1, thereby generating frame images at a plurality of time phases (Step S401). The dynamic imaging is done so that frame images are generated at a plurality of time phases for at least one respiration phase.

During imaging, the imaging technician, via the operation unit 23 of the imaging console 2, inputs the patient information related to the imaged body M, and carries out the operations of specifying the imaging parts, etc. The patient information includes, apart from the name of the imaged body M, that is, the name of the patient, information indicating the attributes of the patient such as the age, sex, weight, height, etc.

In the imaging console 2, the control unit 21 reads out the imaging conditions according to the specified imaging part from the storage unit 22, and sets them as the X-ray irradiation conditions of the radiation source 11 of the imaging device 1, and the image reading conditions in the reading control unit 14. In the following, explanations are given assuming that the imaging technician has specified the lungs (ventilation) as the imaging part. When imaging the lungs in order to view the ventilation function, since the respiration cycle is about 0.3 times per second on an average, for example, the following imaging conditions are set so that it is possible to image frame images at a plurality of time phases for at least one respiration phase.

Frame rate (pulse rate): 2 frames per second (that is, imaging three times per second)
Pixel size: 400 μm
Image size: 40 cm×30 cm
Tube voltage: 120 kV
Tube current: 50 mA
Imaging timing: At every frame interval time period from the timing of changing from inspiration to aspiration (imaging starting timing)

Further, the control unit 21, based on the respiration cycle information detected by the cycle detection device 16, corrects the conditions such as the frame rate, etc. For example, based on the detected respiration cycle, the control unit 21 calculates the frame rate so that one respiration phase is imaged with a prescribed number of frames (for example, 10 frames), and sets the value again. In the example of the above conditions of the frame rate, if the number of respiration cycles detected by the cycle detection device 16 is 0.25 times per second, the frame rate is corrected to 2.5 frames per second.

After setting the imaging conditions, the control unit 21, based on the information of the respiration cycle detected by the cycle detection device 14, makes a judgment of whether or not it is the imaging start timing, that is, whether or not it is the timing of the start of one respiration cycle (for example, the point of time of changing from inspiration to aspiration). If it is the imaging start timing, the control unit 21 starts dynamic imaging by controlling the radiation source 11 and the read control device 14. Further, the control unit 21 counts the time from the start to end of imaging while synchronizing with the start of dynamic imaging.

In the imaging device 1, X-rays are emitted at the prescribed pulse rate according to the set X-ray irradiation conditions. In a similar manner, according to the set image reading conditions, the read control device 14 carries out the X-ray image reading processing from the radiation detection unit 13 at the prescribed frame rate. The control unit 21 synchronizes this X-ray irradiation operation and the image reading operation. Because of this, frame images are generated at a plurality of time phases and are output to the imaging console 2.

In the imaging console 2, the frame images at the different time phases due to dynamic imaging are displayed in the display unit 24 by the display control of the control unit 21. This is for the imaging technician to confirm the image quality, etc. When an approval operation is made by the imaging technician via the operation unit 23, the control unit 21 adds to the frame image at the different time phases the information of the ID for identifying the sequence of images, the patient information, imaging time, etc., and transmits them to the diagnosis console 3. Even in the diagnosis console 3, in a similar manner, a display is made for confirmation (Step S402). Next, when the approval operation is made, the frame images at the different time phases are transmitted to the calculation device 4.

In the calculation device 4, for the frame images of the different time phases, after image processing is carried out by the image processing unit 46 according to the imaging part of the lungs (ventilation), the processing of calculating the estimated ventilation volume is carried out for each of the frames by the image analysis unit 47 (Step S403).

Figure 12:
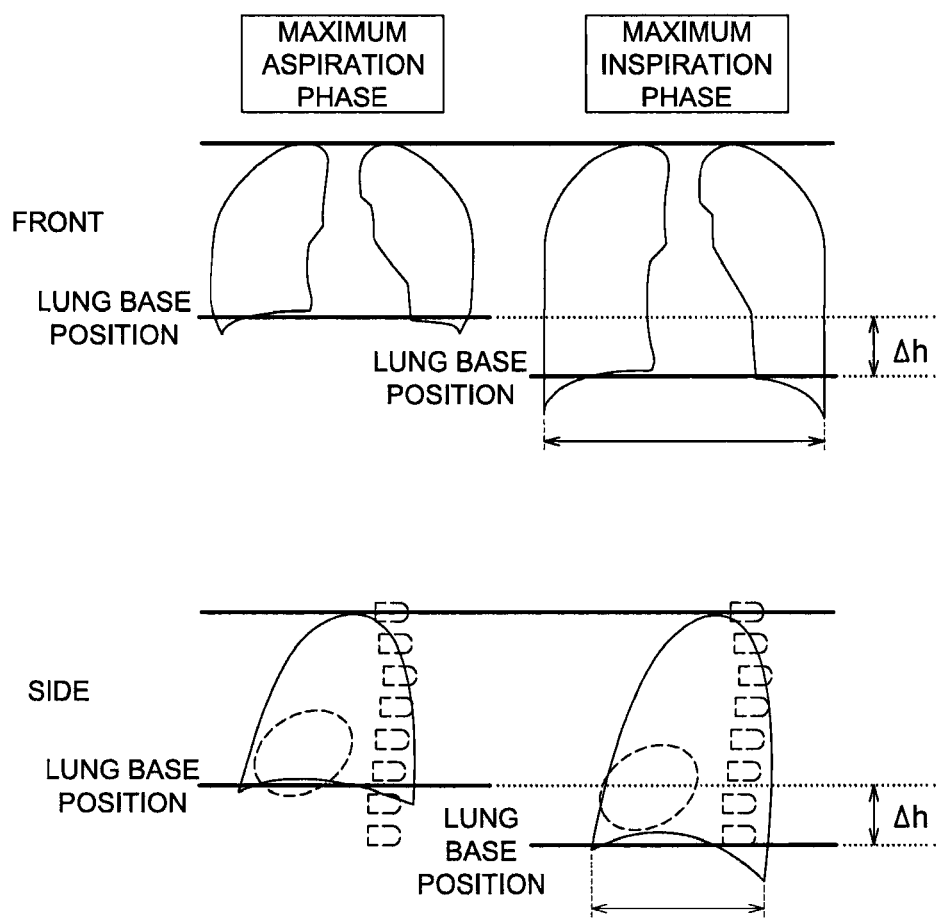
FIG. 12 is a diagram showing the frame images of the maximum aspiratory level and the maximum inspiratory level among the frame images imaged from the front and from the side.

The ventilation volume is the volume of air changed between the maximum aspiration phase (the phase at which air has been exhaled to the maximum extent) and the maximum inspiration phase (the phase at which air has been inhaled to the maximum extent) in one respiration phase as shown in FIG. 12, particularly, in the aspiration phase it is the volume of air exhaled from the maximum inspiration phase to the maximum aspiration phase, and in the inspiration phase it is the volume of air inhaled from the maximum aspiration phase to the maximum inspiration phase.

Due to the expansion and contraction movement of the lower part of the lungs during respiration, the volume of the lungs changes along with changes in the respiration phase. The ventilation volume is the volume of the expanding and contracting part of the lungs, that is, it can be said to be almost equal to the volume of the parts of the lungs that expand and contract between the maximum inspiration phase and the maximum aspiration phase.

Since the volume of the lungs changes mainly due to the lower part of the lungs expanding and contracting in the up-down direction, it is possible to treat the expanding and contracting lung part as a cube with the base of the lung being its bottom surface, and to obtain the volume of the lung part by multiplying the area of the lung part that expands and contracts with the thickness of the lung. In other words, when the length of the base of the lung imaged from the front as shown in FIG. 12 is taken as a, the length of the expanded and contracted lung part is taken as $\Delta h$ taking the position of the lung imaged from the front similarly as the reference, and the thickness of the lung imaged from the side is taken as b, the volume V of the lung that has expanded and contracted between the maximum inspiration phase and the maximum aspiration phase can be obtained by the following equation 1.

Here, the lengths a and $\Delta h$, and the thickness b are obtained by counting the number of pixels.

$$V = a \times b \times \Delta h \tag{1}$$

Further, it is also possible to obtain the volume V according to the following method.

A histogram of the signal values is obtained using the X-ray image imaged from the front. Since a peak region indicating the pulmonary field appears in the histogram, the number of pixels having a signal value corresponding to this peak region of the pulmonary field is counted. This is carried out respectively for the maximum inspiration phase and the maximum aspiration phase, and the difference between the two is obtained. Since this difference corresponds to the area of the lung part that has expanded and contracted between the maximum inspiration phase and the maximum aspiration phase in the X-ray image imaged from the front, it is possible to obtain the volume V by multiplying this difference with the thickness b of the lung imaged from the side.

On the other hand, the signal values of the X-ray image are determined by the amount of X-rays that are transmitted through the imaged body M, and the amount of X-rays transmitted is determined by the thickness of the imaged body M. This is because it becomes more difficult for the X-rays to pass through as the thickness of the imaged body M increases. Therefore, the signal value of the X-ray image is an index indicating the thickness of the lung base of the imaged body M, and if the signal value is changing, it implies that the thickness is changing, that is, it is possible to consider that the volume V of the lung part is changing. In this estimated ventilation volume calculation and display processing, this type of relationship between the signal values of the frame image and the ventilation volume is quantified, and using the quantified value, the estimated ventilation volume is obtained for the time phase of each frame image.

Figure 13:
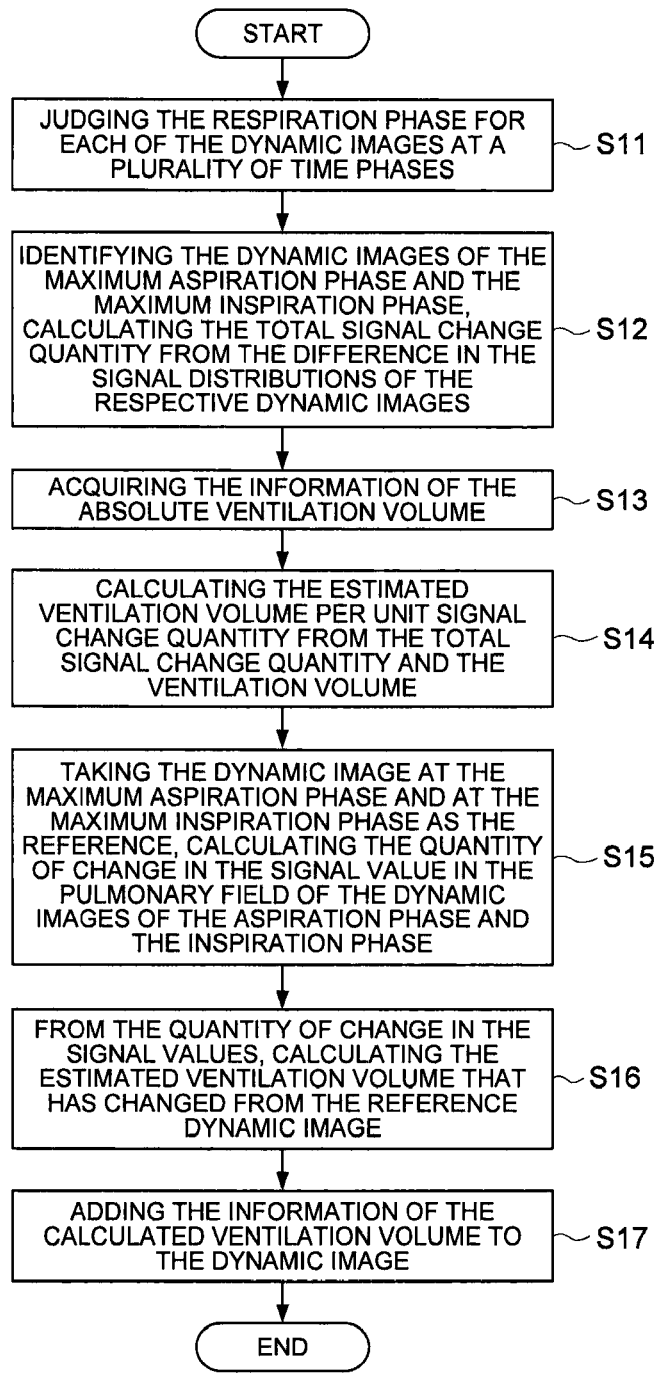
FIG. 13 is a diagram explaining the flow of processing of calculating the estimated ventilation volume.

The processing of calculating the estimated ventilation volume is explained referring to FIG. 13.

Figure 14:
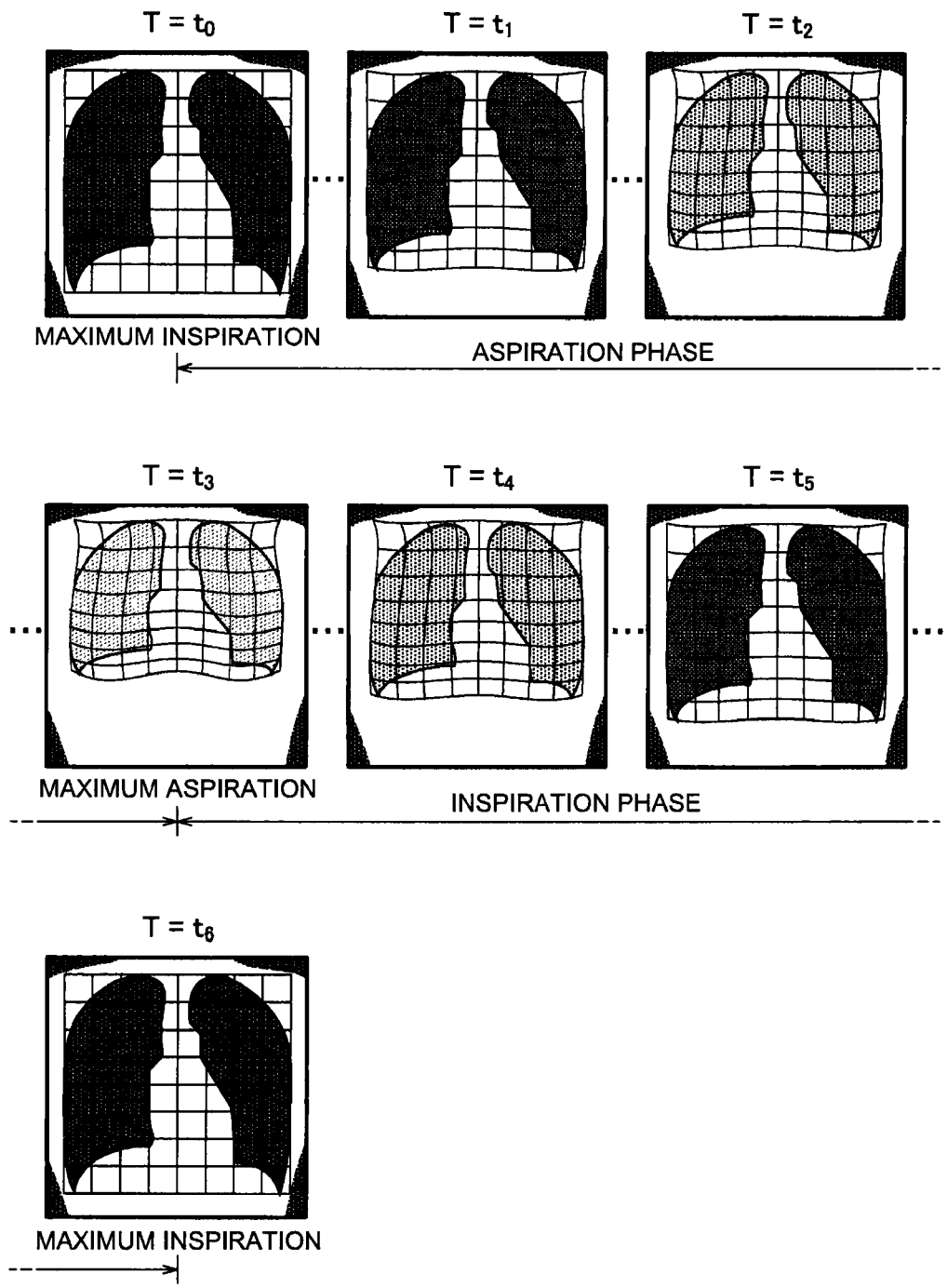
FIG. 14 is a diagram showing the frame images at a plurality of time phases.

As shown in FIG. 13, the image analysis unit 47 judges the respiration phases for each of the frame images in a plurality of time phases (Step S11). Since the lower part of the lungs contracts during inspiration and expands during aspiration, the image analysis unit 47 calculates the area (number of pixels) of the pulmonary field in the frame image related to each time phase, judges the frame images from the time phase when this area becomes a maximum to the time phase when this area becomes a minimum as the frame images belonging to the aspiration phase and the frame images from the time phase when this area becomes a minimum to the time phase when this area becomes a maximum as the frame images belonging to the inspiration phase. In FIG. 14, the result is shown of judging the respiration phase for the frame image of each time phase T (T=$t_0$ to $t_6$).

Further, although it is possible to apply any method for the recognition of the pulmonary field, for example, a threshold value is obtained by discrimination analysis from the histogram of the signal values of a reference image, and a primary detection is made of taking the area with signals higher than this threshold value as the pulmonary field. Next, the edge detection is carried out near the boundary of the region detected in the primary detection, and if the points at which the edge becomes a maximum in the small region near the boundary are extracted along the boundary, it is possible to detect the boundary of the pulmonary field.

Next, the image analysis section 47 judges the frame image in which the area of the pulmonary field becomes a maximum to be the frame image of the maximum inspiration phase, and the frame image in which the area of the pulmonary field becomes a minimum to be the frame image of the maximum aspiration phase. Further, from the difference of the signal distributions of the respective frame images, the quantity of the signal change between the maximum inspiration phase and the maximum aspiration phase (hereinafter referred to as the total signal change quantity) is calculated (Step S12).

It is possible to obtain the signal quantities by preparing the histograms of the frame images.

Figure 15:
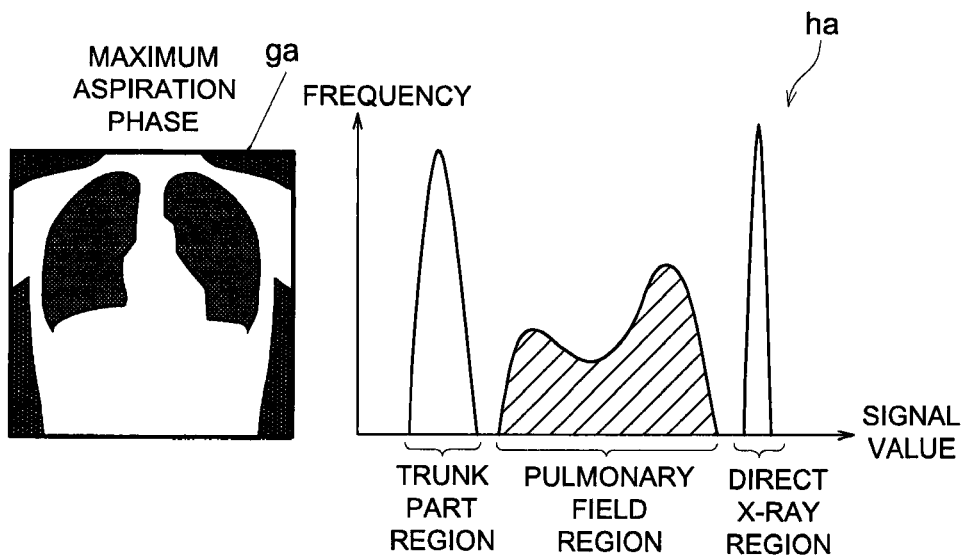
FIG. 15 is an example of the frame images of the maximum aspiratory level and the histogram of their signal values.
Figure 16:
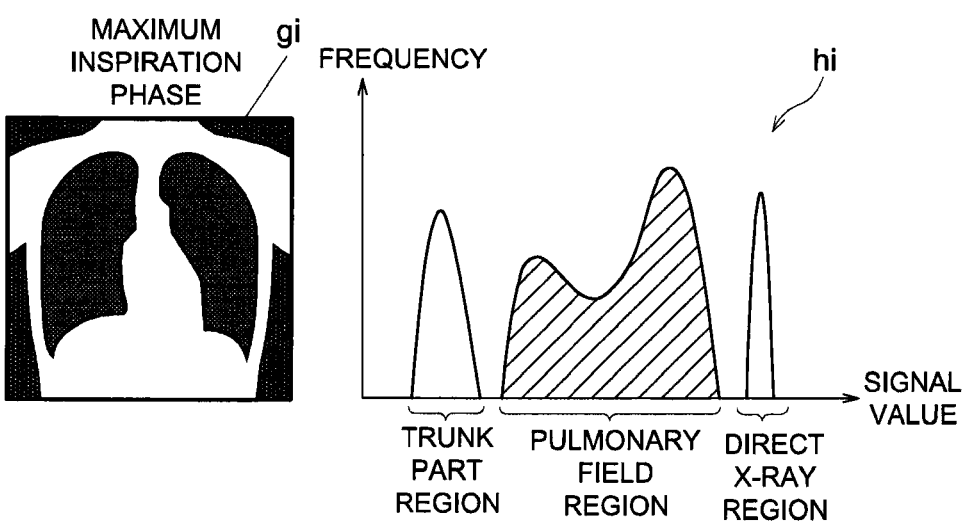
FIG. 16 is an example of the frame images of the maximum inspiratory level and the histogram of their signal values.

FIG. 15 is a diagram showing the frame image ga of the maximum aspiration phase and the histogram ha of its signal values. FIG. 16 is a diagram showing the frame image gi of the maximum inspiration phase and the histogram hi of its signal values. In the histograms ha and hi, broadly dividing, there are three peaks. The peak that appears in the high signal region is the direct X-ray region in which direct X-rays that do not pass through the imaged body M are detected, the peak detected in the low signal region is the peak trunk of the body such as the heart, bones, etc., which have a low X-ray transmittivity. The peak that appears in between them is the pulmonary field of X-rays passing through the lungs.

The signal quantity of the pulmonary field of each of the frames ga and gi corresponds to the area of the signal distribution of the pulmonary field. In other words, it is possible to obtain it by multiplying the signal value constituting the signal distribution of the pulmonary field by its frequency. Since the area of the pulmonary field becomes larger in the maximum inspiration phase, the histogram hi shown in FIG. 16 has a larger area of the signal distribution of the pulmonary field than the pulmonary field in the histogram ha shown in FIG. 15, and it is evident that its signal quantity is large.

Figure 17:
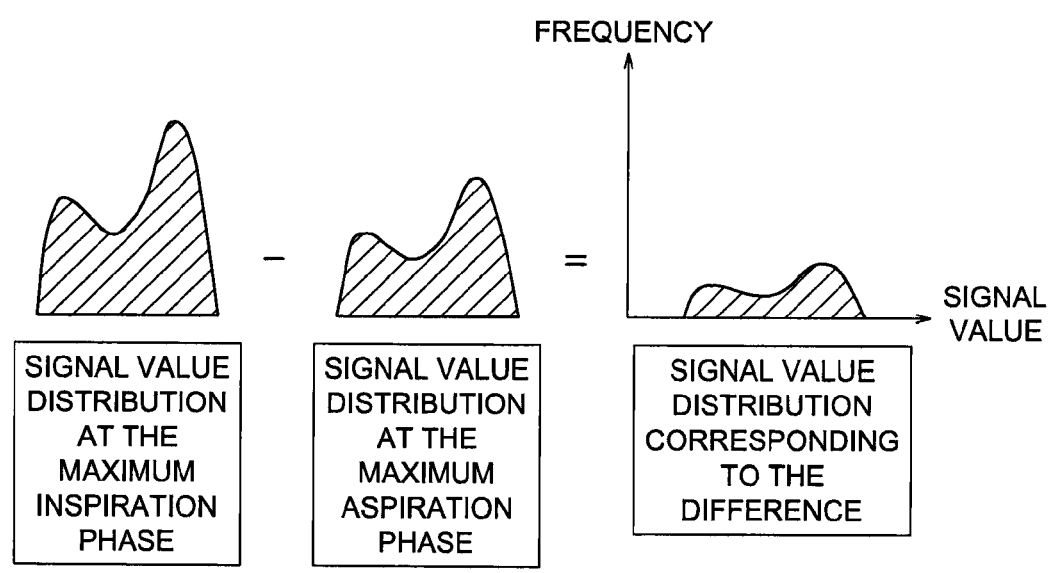
FIG. 17 is a diagram explaining the difference in the signal distribution of the pulmonary field at the maximum aspiratory level and the maximum inspiratory level.

The image analysis unit 47 detects the signal distributions of the pulmonary field in the histograms ha and hi, and calculates the difference between the signal distributions of the respective pulmonary fields as shown in FIG. 17. Regarding the signal distribution which is the calculated difference, the signal quantity obtained by multiplying the signal quantity in the distribution with the frequency, is the signal quantity that has changed between the maximum aspiration phase and the maximum inspiration phase, that is, the total signal change quantity.

Next, the image analysis unit 47 obtains the information of the absolute ventilation volume corresponding to the total signal change quantity (Step S13). The absolute ventilation volume is either the measured value of the ventilation volume or a value that is effectively the same as the measured value of the ventilation volume, and is differentiated from the estimated ventilation volume described later that is estimated by calculations. The information of the absolute ventilation volume can also be made to be obtained from the measured value either by connecting a spirometer, or by the imaging technician inputting the value of the ventilation volume (the ventilation volume of one respiration or the forced vital capacity, etc.,) measured using a spirometer. Or else, it is also possible to carry out dynamic imaging of the imaged body M from the front and from the side as shown in FIG. 13, detecting the lung base from the frame images of the maximum aspiration phase and the maximum inspiration phase, while not only obtaining Δh from the difference with this lung base, but also obtaining the length a and thickness b of the lung base and calculating the volume V, and obtaining it as the absolute ventilation volume. Although the volume V is not a measured value, it is possible to use it as the measured value or a value almost identical to the measured value.

Next, the image analysis unit 47 establishes correspondence between the total signal quantity change and the acquired ventilation volume, assuming that ventilation was done for the absolute ventilation volume (inspiration or expiration) and the signal change was by the amount of the total signal change quantity. Next, from the total signal change quantity and the absolute ventilation volume, the ventilation volume estimated to change when the signal value changes by 1, that is, the estimated ventilation volume per unit signal change quantity is calculated (Step S14).

The estimated ventilation volume per unit signal change quantity is obtained by dividing the absolute ventilation volume into the total signal change quantity. For example, if the obtained absolute ventilation volume is 5000 cc and the total signal change quantity is 10000, the estimated ventilation volume per unit signal change quantity is 5000/10000=0.5. In other words, when the signal quantity changes by 1, it can be estimated that the ventilation volume changes by 0.5 cc.

Next, the image analysis unit 47, taking the frame image of the maximum aspiration phase as the reference, calculates the difference of the signal distribution of the pulmonary field of a frame image belonging to the inspiration phase. In a similar manner, taking the frame image of the maximum inspiration phase as the reference, the difference of the signal distribution of the pulmonary field of a frame image belonging to the aspiration phase is calculated. Next, by obtaining the area of the signal distribution (signal value×frequency) of the signal distribution corresponding to the calculated difference, the quantity of change in the signal value of the pulmonary field from the maximum aspiration phase to the maximum inspiration phase in the respective time phases of aspiration phase and inspiration phase (Step S15).

Once the quantity of change of the signal clause in the different time phases is obtained, the image analysis unit 47, using the estimated ventilation volume per unit signal value change, calculates the estimated ventilation volume that is estimated to have changed from the maximum aspiration phase or from the maximum inspiration phase (Step S16). Explaining the example case in which the estimated ventilation volume per unit signal value change is 0.5 cc, for example, if the frame image at the time phase $T=t_2$ as shown in FIG. 14 belongs to the aspiration phase, and assume that there is a change of only 3000 with respect to the frame image of the maximum inspiration phase (time phase $T=t_0$) at which the signal value of the pulmonary field of that frame image becomes the reference. In this case, the estimated ventilation volume at the time phase $t_2$ is the product of the quantity of change of the signal value and the estimated ventilation volume per unit signal value change, that is, 3000×0.5=1500 cc.

Further, it is possible not only to calculate the estimated ventilation volume of the entire lung from the change in the signal value of the entire pulmonary field region as described above, but also possible to divide the pulmonary field into a plurality of regions and to calculate the estimated ventilation volume for each of these regions.

Figure 18:
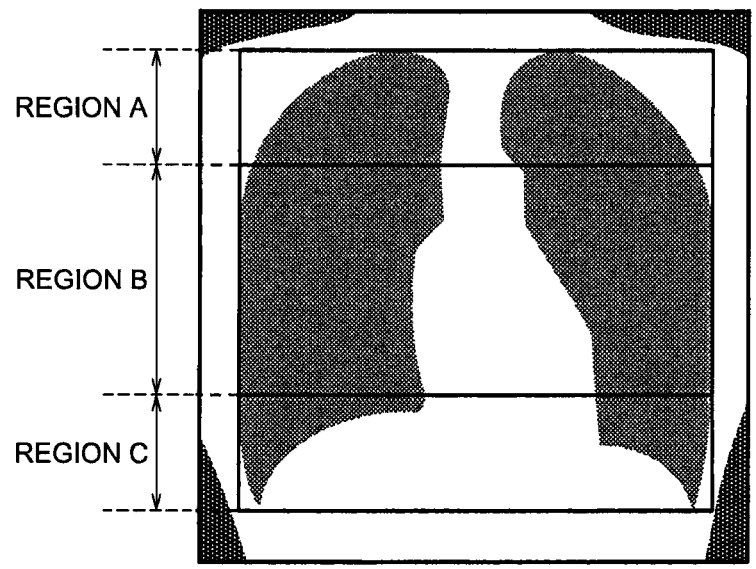
FIG. 18 is a diagram showing an example of dividing the region.
Figure 20:
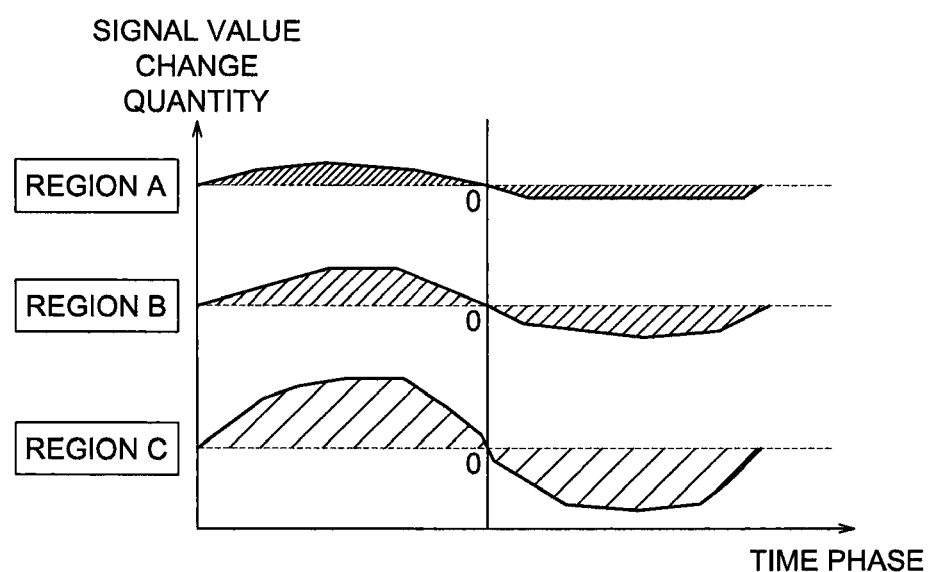
FIG. 20 is a diagram showing the quantity of change in the signal value for each region.

For example, the pulmonary field as shown in FIG. 18 is divided into three regions in the up-down direction naming them as the regions A, B, and C from the top towards the bottom, the signal distributions of the signal values is obtained for each of these regions A, B, and C, and the estimated ventilation volumes are calculated for each of these regions A, B, and C using the method described above. The movement of expansion and contraction is larger in the lower part of a lung and the extent of the expansion and contraction movement of the upper part is small compared to the lower part. Therefore, as shown in FIG. 20, depending on the regions A, B, and C, the quantity of signal change is most small in the top part region A, and is most large in the bottom part region C. In this manner, by calculating the estimated ventilation volume for each of the regions A to C, it becomes possible to obtain the change in the ventilation volume associated with expansion and contraction.

In the above calculation of the estimated ventilation volume, although it is necessary to establish relationship with the regions A, B, and C for each frame image, but this can be carried out by local matching. Local matching is the method of taking a certain frame as the reference and establishing correspondence between the different divided regions obtained by dividing this reference image with the regions of the other frame images having a high level of matching. The level of matching is the extent indicating the matching between the images, and can be obtained by the least squares method, or a correlation function.

Figure 19:
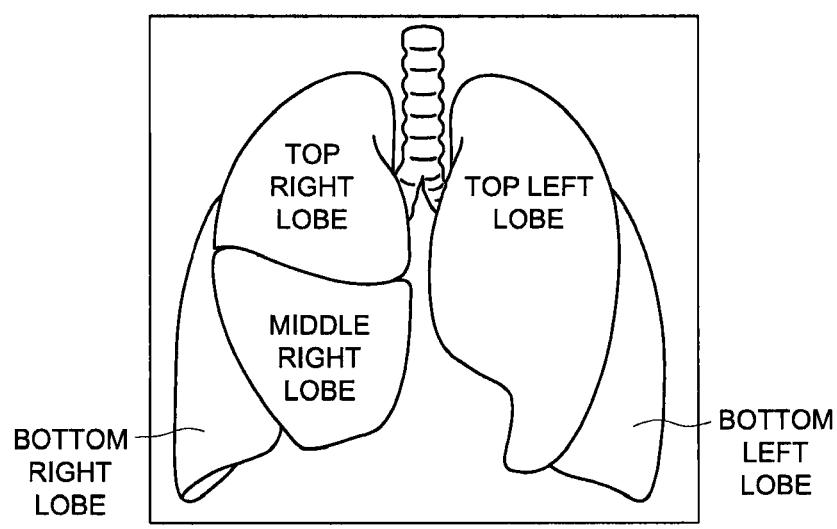
FIG. 19 is a diagram showing an example of dividing the region.

Further, as shown in FIG. 19, it is also possible to divide the pulmonary field in terms of the different anatomical structure parts of the lungs such as the right upper lobe, left upper lobe, etc., and to calculate the estimated ventilation volume for each divided region. In this case, it is possible to obtain the changes in the ventilation volume for each of the anatomical structure parts. At the time of dividing, using a reference image in which the positions and names of the anatomical structure parts have been determined in advance, it is sufficient to recognize and divide into each of the anatomical structure part regions by carrying out image conversion such as by nonlinear warping, etc., so that that reference image and the pulmonary field almost match with each other.

Next, the image analysis unit 47 adds to that frame image the information of not only the calculated estimated ventilation volume per unit signal value change but also the information of the estimated ventilation volume calculated respectively for the frame images of the inspiration phase and the aspiration phase (Step S17). After that, the frame images of the different time phases to which have been added the information of the estimated ventilation volume are transmitted to the image server 5 via the communication unit 45.

In the image server 5, the frame images for the different time phases along with the additional information are stored in the memory in the form of a database. When there is a request from the diagnosis console 3, the image server 5 transmits the set of frame images of the patient related to the request.

As shown in FIG. 11, in the diagnosis console 3, due to the display control by the control unit 31, the frame images of the different time phases received from the image server 5 are displayed in the display unit 34 (Step S404). At this time, the control unit 31 carries out dynamic image display by successively switching the frame image being displayed according to the time phase. The doctor can grasp the dynamic changes according to the respiration movements of the lungs.

Next, the control unit 31, based on the additional information of the displayed frame image, displays the information of the estimated ventilation volume in the display unit 34 (Step S405). In other words, the display is made in the display unit 34 by adding the information of the estimated ventilation volume to each frame image.

Figure 21:
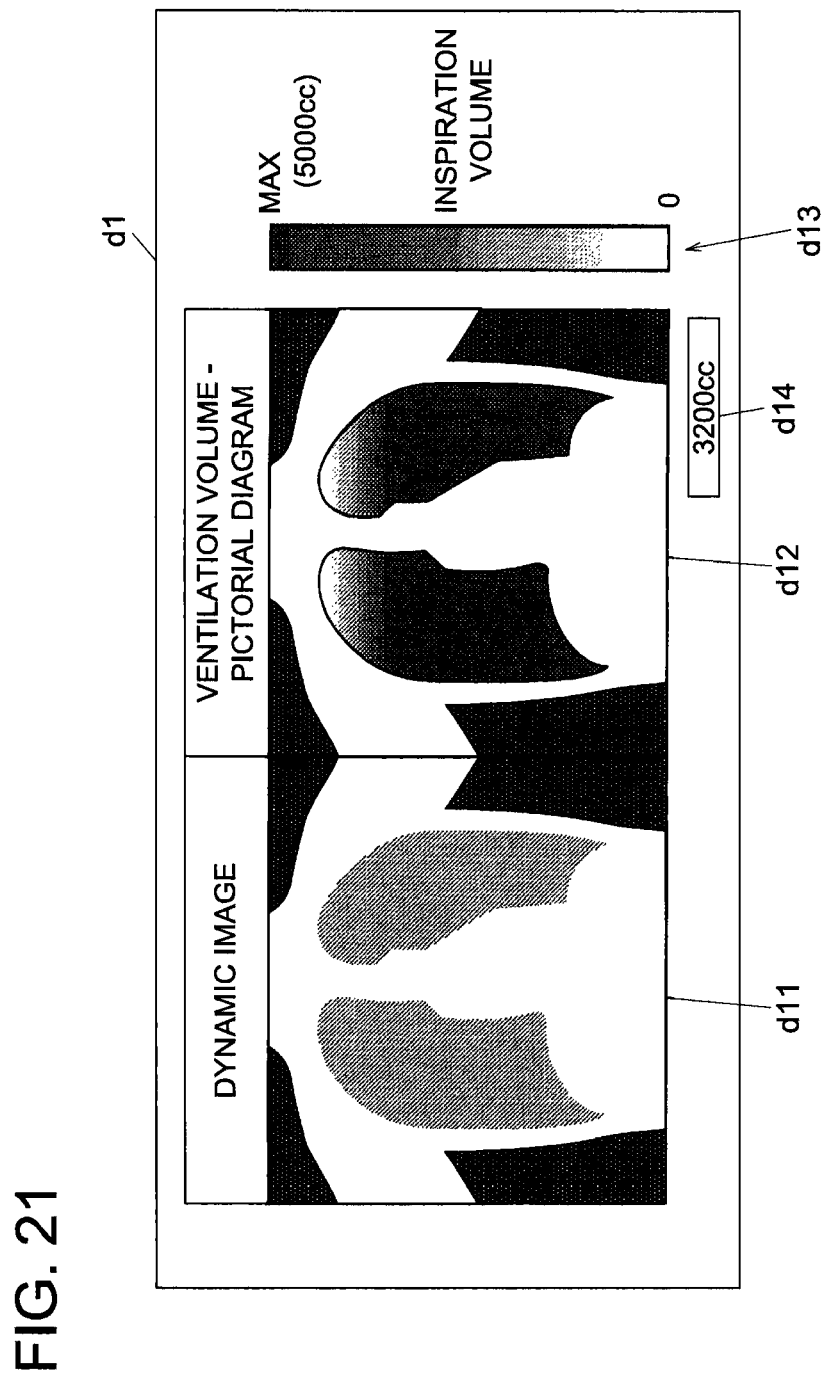
FIG. 21 is an example of the display of the pictorial diagram of frame images and the estimated ventilation volume.

FIG. 21 shows an example of the display of a frame image and an example of the display of the estimated ventilation volume.

In the display screen d1 shown in FIG. 21 are displayed the display area d11 of the frame image and the display area d12 of the estimated ventilation volume. In the display area d11, the control unit 31 displays the different frame images by successively switching them according to the time phase. On the other hand, the in the display area d12 of the estimated ventilation volume, the control unit 31 generates and displays a pictorial diagram showing the estimated ventilation volume calculated for each frame image.

The pictorial diagram showing the estimated ventilation volume is a frame image in which a color is added to the pixel having the signal value used in the calculation of the estimated ventilation volume. In other words, if it is a frame image belonging to the aspiration phase, color is added to the pixel having the signal value constituting the signal distribution corresponding to the difference with the frame image of the maximum inspiration phase, and if it is a frame image belonging to the inspiration phase, color is added to the pixel having the signal value constituting the signal distribution corresponding to the difference with the frame image of the maximum aspiration phase. The color added is different depending on whether the estimated ventilation volume is an aspiration volume or an inspiration volume, and here, an example is explained of a case in which blue color is added when indicating the aspiration volume of a frame image in the aspiration phase, and red color is added when indicating the inspiration volume of a frame image in the inspiration phase.

Figure 22:
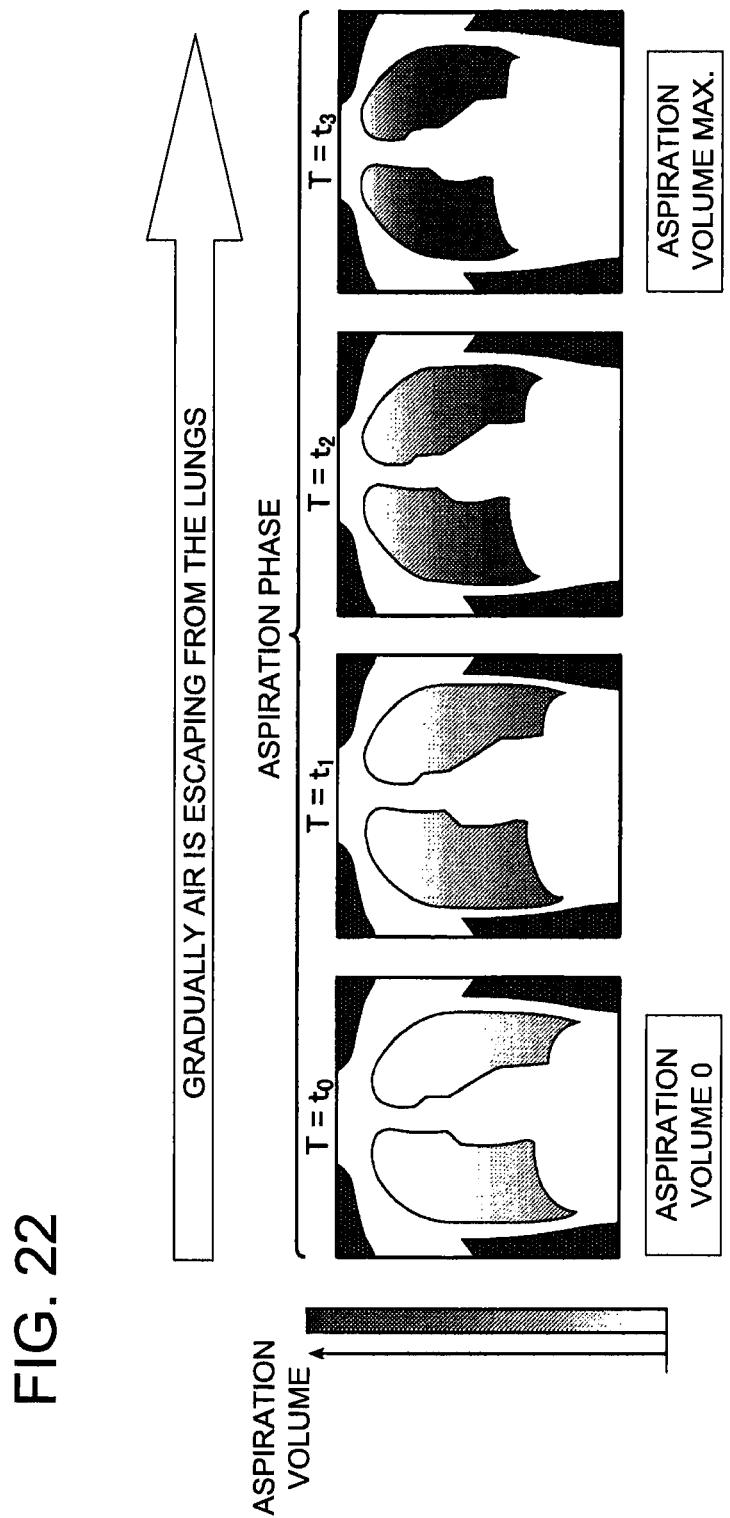
FIG. 22 is a diagram showing a pictorial diagram in the aspiration phase.
Figure 23:
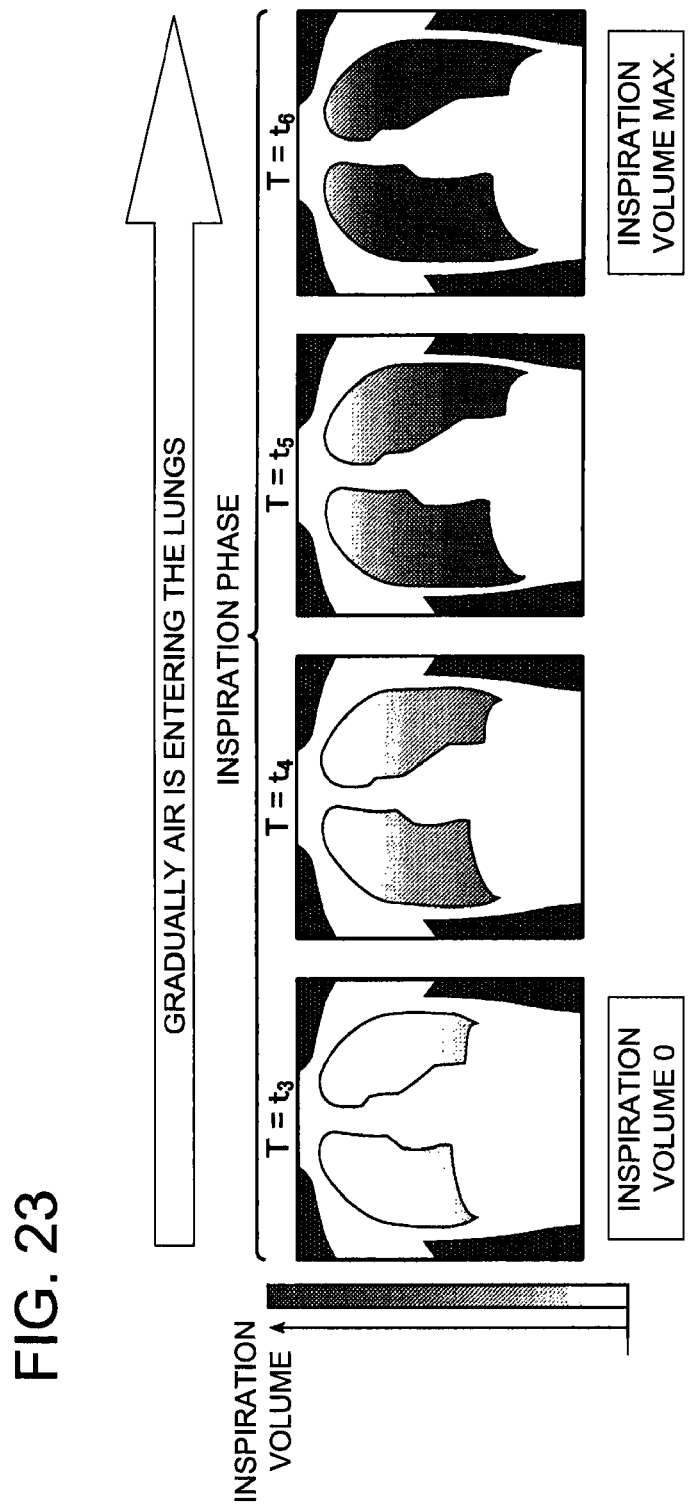
FIG. 23 is a diagram showing a pictorial diagram in the inspiration phase.

FIG. 22 and FIG. 23 show examples of the pictorial drawings showing the estimated ventilation volume. FIG. 22 is the case in which the estimated ventilation volume is an aspiration and FIG. 23 is the case in which the estimated ventilation volume is an inspiration.

As shown in FIG. 22, in the case of the aspiration phase, taking the ventilation volume as 0 of the frame image of the maximum inspiration phase (time phase $T=t_0$), blue color is added to the pixels related to the calculation of the estimated ventilation volume of the frame images of the different time phases $T=t_1, t_2,$ and $t_3$ taking as the reference this frame image of the maximum inspiration phase. By adding blue color, it is possible to show visually the aspiration volume that has changed with reference to the frame image of the maximum inspiration phase.

The case of the inspiration phase is also similar. As shown in FIG. 23, in the case of the inspiration phase, taking the ventilation volume as 0 of the frame image of the maximum aspiration phase (time phase $T=t_3$), red color is added to the pixels related to the calculation of the estimated ventilation volume of the frame images of the different time phases $T=t_4$, $t_5$, and $t_6$ taking as the reference this frame image of the maximum aspiration phase. By adding red color, it is possible to show visually the inspiration volume that has changed with reference to the frame image of the maximum aspiration phase.

The control unit 31 displays the pictorial diagram generated by adding color according to the estimated ventilation volume in each frame image in the display region d12 while successively switching them according to the time phase. Due to the change in the color in the pictorial diagram, it is possible to grasp visually the change in the estimated ventilation volume with the passage of time.

Further, the switching display is made while matching with the time phase of the original frame image in the display region d11. By coupling the dynamic movement with the display of the original frame image, it is possible to refer to the information of the estimated ventilation volume while observing the original frame image.

Since the number of pixels to which the color is added becomes more as the value of the estimated ventilation volume becomes higher, the density of the color in the pictorial diagram becomes an index indicating the extent of the estimated ventilation volume. The control unit 31 displays by the side of the display region d12 an indicator d13 which indicates what density of the color corresponds to what ventilation volume. In the indicator d13, the lower limit of the ventilation volume is displayed as 0, and the upper limit is indicated as "Max" which displays the value of the absolute ventilation volume (for example, 5000 cc, etc.).

In addition, the control unit 31 displays the numerical value of the estimated ventilation volume calculated for each frame image. In concrete terms, as shown in FIG. 21, a display region d14 for displaying the numerical value of the estimated ventilation volume is provided in the bottom part of the display region d12, and the control unit 31 displays in this display region d14 the numerical value of the estimated ventilation volume corresponding to the time phase of the pictorial diagram being displayed currently in the display regions d12.

Further, when a display instruction is made, it is also possible to display the information of the estimated ventilation volume calculated for each region. In this case, the pictorial diagram indicating the estimated ventilation volume can also be displayed with colors added for each region, in the graph shown in FIG. 20, it is possible that the quantity of change in the signal value is replaced with the estimated ventilation volume, the estimated ventilation volume at the maximum aspiration phase and at the maximum inspiration phase is taken as 0, and the estimated ventilation volume at the different time phases are displayed as a graph respectively in the aspiration phase and inspiration phase.

In the above manner, according to the estimated ventilation volume display processing, dynamic imaging is carried out of the chest part of the imaged body M by the imaging device 1, and a plurality of frame images at a plurality of time phases are generated for at lease one respiration phase. On the other hand, the information of the absolute ventilation volume is obtained by the image analysis unit 47 of the calculation device 4, from the total signal change quantity between the maximum aspiration phase and the maximum inspiration phase and from the absolute ventilation volume, the estimated ventilation volume per unit signal change quantity is calculated. In addition, the image analysis unit 47, using the value of the estimated change quantity per unit signal change quantity, calculates the estimated ventilation volumes at the different time phases from the change quantities of the signal values between the frame images at the maximum aspiration phase and the maximum inspiration phase and the frame image at other time phases. In the diagnosis console 3, since the calculated estimated ventilation volume is made to be displayed in the display unit 34 by the control unit 31, it is possible to provide to the doctor the information of the estimated ventilation volume at the different time phases.

Apart from displaying the numerical value of the estimated ventilation volume during the display, since the control unit 31 generates and displays a pictorial diagram indicating the estimated ventilation volume, the doctor can not only grasp the concrete numerical value of the estimated ventilation volume at the different time phases, but can also grasp visually changes in the estimated ventilation volume due to the pictorial diagram.

Further, when calculating and displaying the estimated ventilation volume for each region, the doctor can grasp the estimated ventilation volume that is changing for each region. It is not possible to measure the ventilation volume for each region using a spirometer, etc., and since the information is limited to the ventilation volume of the lungs as a whole, it is possible to provide useful information for diagnosis when detecting the regions where the ventilation function has decreased.

Further, the above estimated ventilation volume calculation and display processing is a desirable example of the present invention, but the present invention is not restricted to this.

For example, in the above estimated ventilation volume calculation and display processing, although the difference of the signal distribution between frame images with neighboring time phases was obtained and the estimated ventilation volume was being calculated, it is not necessary to restrict to this. For example, it is possible to take the frame image of the maximum aspiration phase as the reference in the aspiration phase, and to calculate the estimated ventilation volume from the difference of the signal distribution with this reference frame image, and similarly, it is possible to take the frame image of the maximum inspiration phase as the reference in the inspiration phase, and to calculate the estimated ventilation volume from the difference of the signal distribution with this reference frame image.

Further, although a configuration was explained in which the estimated ventilation volume was displayed in the diagnosis console 3, it is also possible to display in the imaging console 2 or in some other device (such as a PC used for diagnosis, etc.). Further, although a configuration was explained in which a calculation device 4 was provided and the estimated ventilation volume was calculated in the calculation device 4, it is possible to install in the diagnosis console 3 or in some other device a program that calculates the above estimated ventilation volume, and to carry out that calculation.

Further, as a medium that stores the programs related to the processings described above and that can be read by a computer, it is possible to apply, apart from a memory such as a ROM, etc., a portable device such as a DVD, etc. In addition, it also possible to apply a carrier wave as a medium for providing the data of the program via a network.

What is claimed is:

1. A dynamic image processing system comprising:
an imaging unit that carries out dynamic imaging of a target part of a human body under examination and generates a plurality of frames of images indicating a dynamic condition of the target part of the human body under examination;
a calculation unit that calculates from said frames of images a dynamic feature amount of the target part of the human body under examination;
a display unit that displays on a display screen the plurality of frames of images; and
a display control unit that displays at least one of the plurality of frames of images and the calculated dynamic feature amount on the display screen concurrently;
wherein said display control unit, according to a result of calculation of the dynamic feature amount by said calculation unit adds information to at least one among the plurality of frames of images, or modifies a part of at least one among the plurality of frames of images, and displays on said display screen;
wherein said display control unit, according to the result of calculation of the dynamic feature amount by the calculation unit colors at least one frame of image among the plurality of frames of images and displays on the display screen;
wherein said display control unit has a dynamic image display mode for a motion display of the plurality of frames of images indicating a dynamic condition on the display screen, and a still image display mode for a still image display of the plurality of frames of images indicating a dynamic condition arranging the plurality of frame of images next to one another on the display screen, and
wherein the dynamic image processing system is provided with an operation unit for selecting the dynamic image display mode or the still image display mode;
wherein said calculation unit calculates, as the dynamic feature amount, an area ratio of an image region of the target part under examination between neighboring frame images among the plurality of frames of images in the imaging sequence; and
said display control unit, when the dynamic image display mode is selected, displays a motion image of the plurality of frames of images indicating dynamic condition on the display screen, and colors the frame image currently being displayed in the motion image according to the area ratio calculated by said calculation unit between the frame image currently being displayed and a frame image imaged immediately prior to it and displays the colored frame image alongside the motion image being displayed.

2. A dynamic image processing system comprising:
an imaging unit that carries out dynamic imaging of a target part of a human body under examination and generates a plurality of frames of images indicating a dynamic condition of the target part of the human body under examination;
a calculation unit that calculates from said frames of images a dynamic feature amount of the target part of the human body under examination;
a display unit that displays on a display screen the plurality of frames of images; and
a display control unit that displays at least one of the plurality of frames of images and the calculated dynamic feature amount on the display screen concurrently;
wherein said display control unit, according to a result of calculation of the dynamic feature amount by said calculation unit adds information to at least one among the plurality of frames of images, or modifies a part of at least one among the plurality of frames of images, and displays on said display screen;
wherein said display control unit, according to the result of calculation of the dynamic feature amount by the calculation unit colors at least one frame of image among the plurality of frames of images and displays on the display screen;
wherein said display control unit has a dynamic image display mode for a motion display of the plurality of frames of images indicating a dynamic condition on the display screen, and a still image display mode for a still image display of the plurality of frames of images indicating a dynamic condition arranging the plurality of frame of images next to one another on the display screen, and
wherein the dynamic image processing system is provided with an operation unit for selecting the dynamic image display mode or the still image display mode
wherein said calculation unit, among the plurality of frames of images, extracts a frame image with a maximum area of an image region of the target part under examination and a frame image with a minimum area of an image region of the target part, and calculates as the feature amount the area ratio of the image region of the target part between the extracted frame images; and
wherein said display control unit, when the dynamic image display mode is selected, not only displays a motion image of the plurality of frames of images indicating dynamic condition on the display screen, but also colors the frame image with the maximum area or the frame image with the minimum area according to the area ratio calculated by said calculation unit and displays the colored frame image alongside the motion image being displayed.

3. A dynamic image processing system comprising:
an imaging unit that carries out dynamic imaging of a target part of a human body under examination and generates a plurality of frames of images indicating a dynamic condition of the target part of the human body under examination;
a calculation unit that calculates from said frames of images a dynamic feature amount of the target part of the human body under examination;
a display unit that displays on a display screen the plurality of frames of images; and
a display control unit that displays at least one of the plurality of frames of images and the calculated dynamic feature amount on the display screen concurrently;
wherein said display control unit, according to a result of calculation of the dynamic feature amount by said calculation unit adds information to at least one among the plurality of frames of images, or modifies a part of at least one among the plurality of frames of images, and displays on said display screen;
wherein said display control unit, according to the result of calculation of the dynamic feature amount by the calculation unit colors at least one frame of image among the plurality of frames of images and displays on the display screen;
wherein said display control unit has a dynamic image display mode for a motion display of the plurality of frames of images indicating a dynamic condition on the display screen, and a still image display mode for a still image display of the plurality of frames of images indicating a dynamic condition arranging the plurality of frame of images next to one another on the display screen, and wherein the dynamic image processing system is provided with an operation unit for selecting the dynamic image display mode or the still image display mode, wherein said calculation unit calculates, as the dynamic feature amount, an area ratio of an image region of the target part under examination between neighboring frame images among the plurality of frames of images in the imaging sequence;

said operation unit is configured so that, when the still image display mode is selected, in addition, it is possible to specify one frame image among the plurality of frames of images displayed next to one another; and said display control unit, when the still image display mode is selected, makes a still image display of the plurality of frames of images indicating the dynamic motion arranged next to one another and, and colors and displays the specified frame image with a color corresponding to the area ratio calculated by said calculation unit between the frame image and a frame image imaged immediately prior to it.

4. A dynamic image processing system comprising:

an imaging unit that carries out dynamic imaging of a target part of a human body under examination and generates a plurality of frames of images indicating a dynamic condition of the target part of the human body under examination;

a calculation unit that calculates from said frames of images a dynamic feature amount of the target part of the human body under examination;

a display unit that displays on a display screen the plurality of frames of images; and a display control unit that displays at least one of the plurality of frames of images and the calculated dynamic feature amount on the display screen concurrently;

wherein said display control unit, according to a result of calculation of the dynamic feature amount by said calculation unit, adds information to at least one among the plurality of frames of images, or modifies a part of at least one among the plurality of frames of images, and displays on said display screen;

wherein said display control unit, according to the result of calculation of the dynamic feature amount by the calculation unit, colors at least one frame of image among the plurality of frames of images and displays on the display screen;

wherein said calculation unit calculates, as the dynamic feature amount, an area ratio of an image region of the target part under examination between neighboring frame images among the plurality of frames of images in the imaging sequence; and said display control unit displays a motion image of the plurality of frames of images indicating dynamic condition on the display screen, and colors the frame image currently being displayed in the motion image according to the area ratio calculated by said calculation unit between the frame image currently being displayed and a frame image imaged immediately prior to it and displays the colored frame image alongside the motion image being displayed.

5. A dynamic image processing system comprising:

an imaging unit that carries out dynamic imaging of a target part of a human body under examination and generates a plurality of frames of images indicating a dynamic condition of the target part of the human body under examination;

a calculation unit that calculates from said frames of images a dynamic feature amount of the target part of the human body under examination;

a display unit that displays on a display screen the plurality of frames of images; and a display control unit that displays at least one of the plurality of frames of images and the calculated dynamic feature amount on the display screen concurrently;

wherein said display control unit, according to a result of calculation of the dynamic feature amount by said calculation unit, adds information to at least one among the plurality of frames of images, or modifies a part of at least one among the plurality of frames of images, and displays on said display screen;

wherein said display control unit, according to the result of calculation of the dynamic feature amount by the calculation unit, colors at least one frame of image among the plurality of frames of images and displays on the display screen;

wherein said calculation unit, among the plurality of frames of images, extracts a frame image with a maximum area of an image region of the target part under examination and a frame image with a minimum area of an image region of the target part, and calculates as the feature amount the area ratio of the image region of the target part between the extracted frame images; and said display control unit displays a motion image of the plurality of frames of images indicating dynamic condition on the display screen of the display unit, and colors frame image with a maximum area of an image region of the target part under examination or the frame image with a minimum area of an image region of the target part according to the area ratio calculated by said calculation unit and displays the colored frame image alongside the motion image being displayed.

6. A dynamic image processing system comprising:

an imaging unit that carries out dynamic imaging of a target part of a human body under examination and generates a plurality of frames of images indicating a dynamic condition of the target part of the human body under examination;

a calculation unit that calculates from said frames of images a dynamic feature amount of the target part of the human body under examination;

a display unit that displays on a display screen the plurality of frames of images; and a display control unit that displays at least one of the plurality of frames of images and the calculated dynamic feature amount on the display screen concurrently; and an operation unit;

wherein said display control unit, according to a result of calculation of the dynamic feature amount by said calculation unit, adds information to at least one among the plurality of frames of images, or modifies a part of at least one among the plurality of frames of images, and displays on said display screen;

wherein said display control unit, according to the result of calculation of the dynamic feature amount by the calculation unit, colors at least one frame of image among the plurality of frames of images and displays on the display screen;

wherein said calculation unit calculates, as the dynamic feature amount, an area ratio of an image region of the target part under examination between neighboring frame images among the plurality of frames of images in the imaging sequence; and wherein said display control unit makes a still image display of the plurality of frames of images indicating the dynamic motion arranged next to one another and, and colors and displays the frame image specified by the operation unit with a color corresponding to the area ratio calculated by said calculation unit between the frame image and a frame image imaged immediately prior to it.

7. The dynamic image processing system of claim 1, wherein said display control unit reduces the sizes of the plurality of frames of images and displays them in the display screen of said display unit.

8. A dynamic image processing system comprising:

an imaging unit that carries out dynamic imaging of a target part of a human body under examination and generates a plurality of frames of images indicating a dynamic condition of the target part of the human body under examination;

a calculation unit that calculates from said frames of images a dynamic feature amount of the target part of the human body under examination;

a display unit that displays on a display screen the plurality of frames of images; and a display control unit that displays at least one of the plurality of frames of images and the calculated dynamic feature amount on the display screen concurrently;

wherein said display control unit, according to a result of calculation of the dynamic feature amount by said calculation unit, adds information to at least one among the plurality of frames of images, or modifies a part of at least one among the plurality of frames of images, and displays on said display screen;

wherein said display control unit, according to the result of calculation of the dynamic feature amount by the calculation unit, colors at least one frame of image among the plurality of frames of images and displays on the display screen;

wherein the plurality of frames of images is frames showing a dynamic motion of a chest part including a pulmonary field; and said calculation unit calculates a ventilation ratio of the pulmonary field by calculating as the feature amount the area ratio between the plurality of frames of images.

9. A dynamic image processing system comprising:

an imaging unit that carries out dynamic imaging of a target part of a human body under examination and generates a plurality of frames of images indicating a dynamic condition of the target part of the human body under examination;

a calculation unit that calculates from said frames of images a dynamic feature amount of the target part of the human body under examination;

a display unit that displays on a display screen the plurality of frames of images; and a display control unit that displays at least one of the plurality of frames of images and the calculated dynamic feature amount on the display screen concurrently;

wherein said display control unit, according to a result of calculation of the dynamic feature amount by said calculation unit, adds information to at least one among the plurality of frames of images, or modifies a part of at least one among the plurality of frames of images, and displays on said display screen wherein said imaging unit carries out dynamic imaging of a chest region of a human body and generates for at least one respiration phase a plurality of frames of images indicating a dynamic condition in a plurality of time phases, wherein said calculation unit, acquires information of an absolute ventilation volume between a maximum aspiratory level and a maximum inspiratory level during the respiration phase, calculates an estimated ventilation volume per unit change quantity of a signal from the absolute ventilation volume and a quantity of signal value change between the dynamic image of the maximum aspiratory level and the dynamic image of the maximum inspiratory level among the generated plurality of frames of images indicating a dynamic condition, using a value of the estimated ventilation volume per unit change quantity in the signal calculates each estimated ventilation volume at each time phase, and wherein said display control unit displays in said display unit the calculated each estimated ventilation volume for each time phase.

10. The dynamic image processing system of claim 9, wherein said display control unit displays a numerical value indicating the calculated estimated ventilation volume.

11. The dynamic image processing system of claim 9, wherein said display control unit generates a pictorial image indicating the calculated estimated ventilation volume in the pulmonary field region in each frame of images indicating dynamic condition, and displays the pictorial images by switching them successively according to the time phase.

12. The dynamic image processing system of claim 9, wherein said calculation unit divides the pulmonary field region included in the dynamic images into a plurality of regions, and calculates the estimated ventilation volume for each of these divided regions, and wherein said display control unit displays said estimated ventilation volume calculated for each of said divided regions in said dynamic images.

* * * * *